United States Patent [19]

Andersson et al.

[11] Patent Number: 5,639,778
[45] Date of Patent: Jun. 17, 1997

[54] INDOLETETRALINS HAVING DOPAMINERGIC ACTIVITY

[75] Inventors: Bengt R. Andersson; Per A. E. Carlsson; Lars O. Hansson; Clas A. Sonesson, all of Goteborg; N. Peter Stjernlof, Vastra Frolunda, all of Sweden; Kjell A. I. Svensson, Portage, Mich.; R. Nicholas Waters, Goteborg, Sweden; Susanne R. Haadsma-Svensson, Portage, Mich.

[73] Assignee: Pharmacia & Upjohn Company, Kalamazoo, Mich.

[21] Appl. No.: 522,290

[22] PCT Filed: Mar. 21, 1994

[86] PCT No.: PCT/US94/02800

§ 371 Date: Sep. 7, 1995

§ 102(e) Date: Sep. 7, 1995

[87] PCT Pub. No.: WO94/21608

PCT Pub. Date: Sep. 29, 1994

Related U.S. Application Data

[63] Continuation-in-part of Ser. No. 37,568, Mar. 25, 1993, abandoned.

[51] Int. Cl.$^6$ .................. A61K 31/33; C07D 491/04; C07D 409/12
[52] U.S. Cl. .................. 514/411; 548/427; 548/432; 548/437
[58] Field of Search ............... 514/411; 548/432, 548/437, 427

[56] References Cited

U.S. PATENT DOCUMENTS

| | | | |
|---|---|---|---|
| 4,060,626 | 11/1977 | Hrstka et al. | 424/274 |
| 4,110,339 | 8/1978 | Bach et al. | 260/326.9 |
| 4,470,990 | 9/1984 | Asselin et al. | 548/425 X |
| 4,510,157 | 4/1985 | Asselin et al. | 514/411 |

FOREIGN PATENT DOCUMENTS

| | | | |
|---|---|---|---|
| 0 055 043 | 1/1985 | European Pat. Off. | C07D 209/60 |
| 0286515 | 10/1988 | European Pat. Off. | |
| 0286516 | 10/1988 | European Pat. Off. | |
| 27 40 836 | 9/1977 | Germany | C07D 491/04 |

OTHER PUBLICATIONS

Nichols, D.E. et al, *J. Med. Chem.*, 1989, 32, 2128–34.
Shagalov, L.B. et al., "Vilsmeier reaction in angular tetrahydrobenzindoles," *Khim. Geterotsikl. Soedin.* 3:360–65 (1979) (Russ.) – Chem. Abstr. 91:56747v.
Shagalov, L.B. et al., "Synthesis of angular tetrahydro[4,5]- and [6,7]benzindoles," *Khim. Geterotsikl. Soedin.* 5:634–40 (1978) (Russ.) – Chem. Abstr. 89:146703r.

*Primary Examiner*—Jacqueline Haley
*Attorney, Agent, or Firm*—Donald L. Corneglio

[57] ABSTRACT

A compound of formula (I) and pharmaceutically acceptable salts thereof, where Z is $R_3$ and X and Y form (a), or X is $R_3$ and Y and Z form (a) or (b); $R_1$ and $R_2$ are independently hydrogen, $C_{1-6}$ alkyl, $C_{3-7}$ cycloalkyl, —$CH_2$—$C_{3-7}$ cycloalkyl, phenyl (optionally substituted with halogen or $C_{1-6}$ alkyl), -thiophenyl (optionally substituted with halogen or $C_{1-6}$ alkyl), or $C_{1-6}$ alkyl phenyl; $R_3$ are independently hydrogen, halogen, —O—$C_{1-6}$ alkyl or $C_{1-6}$ alkyl; $R_4$ is a valence bond, $CH_2$ or oxygen; $R_5$ and $R_6$ are independently hydrogen, sulfur, —S—$C_{1-6}$ alkyl, halogen, $CON(R_3)_2$, —$COCF_3$, —CO—$C_{1-6}$ alkyl, —CO phenyl, oxygen, —CHO, CN except that when Y and Z form (b), $R_1$ and $R_2$ are hydrogen or a $C_{1-6}$ alkyl and $R_3$ is hydrogen, then at least one of $R_5$ and $R_6$ must be other than hydrogen. These compounds and derivatives thereof exhibit dopamine-receptor stimulating activity in mammals.

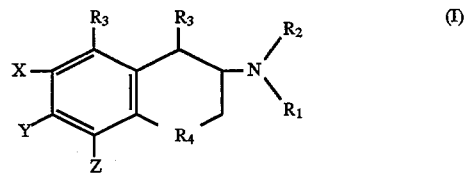

(I)

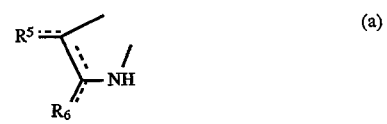

(a)

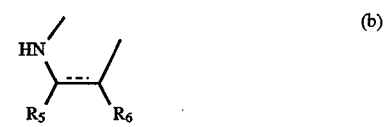

(b)

9 Claims, No Drawings

INDOLETETRALINS HAVING DOPAMINERGIC ACTIVITY

CROSS-REFERENCE TO RELATED APPLICATIONS

This application is the U.S. national phase of PCT/US94/02800 filed 21 Mar. 1994, published as WO94/21608, which was a continuation-in-part of U.S. Ser. No. 08/037,568 filed 25 Mar. 1993, abandoned.

BACKGROUND OF THE INVENTION

This invention relates to novel 6,7,8,9-tetrahydro-3H-benz(e)indolamine derivatives, to therapeutically acceptable acid addition salts thereof, to processes for their preparation and intermediates used therein, to methods of using the derivatives and to pharmaceutical compositions of the derivatives. These derivatives exhibit dopamine-receptor stimulating activity in a mammal. Thus, they can be useful for treating hyperprolactinemia, glactorrhea, amenorrhea, impotence, schizophrenia, Parkinsonism, diabetes, acromegaly, hypertension and other central nervous system disorders which respond to dopamine-receptor stimulation.

A number of 6,7,8,9-tetrahydro-3H-benz(e)indolamine derivatives are known and described, for example, L. B. Shagalov et al., Chem. Abstr. 91, 56747 v (1979) for Khim. Geterotsikl. Siedin., (3), 360 (1979); L. B. Shagalov et al., Chem. Abstr. 89, 146703 r (1978) for Khim. Geterotsikl. Soedin., (5), 634 (1978); Derwent Publicatiions Ltd., Farmdoc 46000U for Netherlands Patent 7,300,871, published Jul. 30, 1973; and Derwent Publications Ltd., Farmdoc 24087B for German Offenlegungsschrift 2,740,836, published Mar. 22, 1979. The reported compounds lack the particular substitutents of the indole ring system which are characteristic of the compounds of this invention as well as the various placements of the indole ring structure. N. J. Bach and E. C. Kornfeld, U.S. Pat. No. 4,110,339, Aug. 29, 1978, disclose tricyclic tetrahydro-2H-benz(c)pyrroles which are dopamine agonist. These latter compounds are distinguished most readily from the compounds of this invention by having a perfused tricyclic ring system.

European Patent 0055043-B1 discloses 6,7,8,9-tetrahydro-3H-benz(e) indole compounds (see, also U.S. Pat. Nos. 4,510,157 and 4,470,990); however, they lack the indole and/or tertiary amine substitutents of this invention. Alternate placement of the indole ring is not disclosed by this reference.

SUMMARY OF THE INVENTION

In one aspect the subject invention is directed toward compounds of Formula I and pharmaceutically acceptable salts thereof:

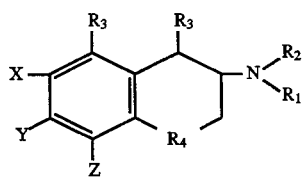

where Z is $R_3$ and X and Y form (a), or X is $R_3$ and Y and Z form (a), (b) or (c)

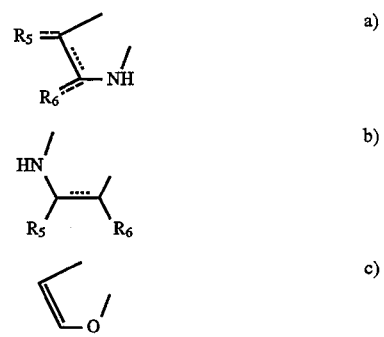

$R_1$ and $R_2$ are independently hydrogen, $C_{1-6}$ alkyl, $C_{3-7}$ cycloalkyl, —$CH_2$—$C_{3-7}$ cycloalkyl, phenyl (optionally substituted with halogen or $C_{1-6}$ alkyl), -thiophenyl (optionally substituted with halogen or $C_{1-6}$ alkyl), or $C_{1-6}$ alkyl phenyl;

$R_3$ are independently hydrogen, halogen, —O—$C_{1-6}$ alkyl or $C_{1-6}$ alkyl;

$R_4$ is a valence bond, $CH_2$ or oxygen;

$R_5$ and $R_6$ are independently hydrogen, sulfur, —S—$C_{1-6}$ alkyl, halogen, $CON(R_3)_2$, —$COCF_3$, —CO—$C_{1-6}$ alkyl, —CO phenyl, oxygen, —CHO, CN except that when Y and Z form (b), $R_1$ and $R_2$ are hydrogen or a $C_{1-6}$ alkyl and $R_3$ is hydrogen, then at least one of $R_5$ and $R_6$ must be other than hydrogen or oxygen. These compounds and derivatives thereof predominantly exhibit dopamine-receptor stimulating activity in mammals.

DETAILED DESCRIPTION OF THE INVENTION

The compounds of this invention are represented by Formula I or a pharmaceutically acceptable salt thereof as shown above. The compounds provide a method for treating mammals, especially humans, suffering from dopamine generated central nervous system disorders by administering a therapeutically effective amount of Formula I.

In the structural Formula I, the carbon content of various hydrocarbon-containing moieties is indicated by a prefix designating the minimum and maximum number of carbon atoms in the moiety, i.e., the prefix $C_i$–$C_j$ defines the number of carbon atoms present from the integer "i" to "j" inclusive. Thus, $C_1$–$C_6$ alkyl refers to straight and branched alkyls of one to six carbon atoms, inclusive, including isomers thereof such as methyl, propyl, ethyl and isopropyl.

Cycloalkyl are three to seven carbon atoms such as cyclopropyl, cyclobutyl, cyclopentyl and cyclohexyl.

The term "halogen" includes fluoro, chloro, bromo and iodo.

Pharmaceutically acceptable salts means salts useful for administering the compounds of this invention or useful forms the compounds may take in vitro and in vivo and include potassium, sodium, hydrochloride, hydrobromide, hydroiodide, sulfate, phosphate, acetate, propionate, lactate, mesylate, maleate, malonate, succinate, tartrate, citrate and the like. These salts may be in hydrated form.

A pharmaceutical composition is provided by admixing the compound of Formula I, or or a therapeutically acceptable acid addition salt thereof, with a pharmaceutically acceptable carrier.

The exact dosage and frequency of administration depends on the particular condition being treated, the severity of the condition being treated, the age, weight, general physical condition of the particular patient, other medication the individual may be taking as is well known to those skilled in the art.

Thus, the subject compounds, along with a pharmaceutically-acceptable carrier, diluent or buffer, can be administrated in a therapeutic or pharmacological amount effective to alleviate the central nervous system disorder with respect to the physiological condition diagnosed. The compounds can be administered intravenously, intramuscularly, topically, transdermally such as by skin patches, buccally or orally to man or other vertebrates.

The compositions of the present invention can be presented for administration to humans and other vertebrates in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other insert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

The compounds of this invention are used to stimulate dopamine receptors in a mammal in need thereof by administering to the mammal an effective dopamine receptor stimulating amount of a compound of Formula I or a therapeutically acceptable acid addition salt thereof. The compounds of this invention are favorably used in combination with an effective amount of an agent commonly used in the treatment of Parkinsonism and related disorders, particularly those selected from bromocriptine, lergotrile, levodopa, combination of levodopa and carbidopa, L-propyl-L-leucylglycinamide and L-propyl-N-methyl-D-leucylglycinamide.

The compounds of this invention may be obtained by one of the following methods described below and outlined in the appropriate charts. For clarity, the numerical charts (1–3) describe the last steps leading to the exemplified final products while the alphanumerical charts describe routes to desired starting material to be used in the final steps.

EXAMPLE 1

7-Di-n-propylamino-6,7,8,9-tetrahydro-1H-benzo[g]indole-2,3-dione (2a, Chart 1) ($R_1R_2$ n-propyl; $R_3$ hydrogen; $R_4$ $CH_2$; YZ (a); $R_5R_6$ O)

A solution of 5-amino-2-di-n-propylamino-1,2,3,4-tetrahydronaphthylenee dihydrochloride (1a, Chart 1, preparation see, Stjernlof et al., Eur. J. Med. Chem. 1993) (35 g, 0.11 mol), chloral hydrate (19.4, 0.12 mol), hydroxylamine hydro-chloride (23.6, 0.34 mol) and sodium sulfate (119.4 g, 0.84 mol) in 445 mL water was refluxed for 1 hour under an inert atmosphere. After cooling, diluted ammonia was added to basify. The aqueous solution was extracted three times (ethyl acetate). The combined organic extracts were dried (sodium sulfate), filtered and evaporated to yield 30 g of the intermediate oxime, which was refrigerated and dissolved in freezer cold 90% sulfuric acid (510 mL). The resulting solution was stirred at ambient temperature in an inert atmosphere for 0.5 hour and was then heated at 80° C. for 0.5 hour. The solution was allowed to reach ambient temperature within an hour and was then poured on crushed ice. Ethyl acetate and diluted ammonia (until pH 8–9) was added and the mixture was shaken. The aqueous phase was extracted 4 times (ethyl acetate) and the combined organic phases were dried (magnesium sulfate), filtered and evaporated to yield 23.5 g. (71%) of the reddish oil, which was sufficiently pure for further synthesis. For analytical and biological purposes, smaller amounts of the material was chromatographed on silica (acetone/methanol, 20:1) to afford an orange solid. m.p. 173°–177° C.

EXAMPLE 2

Di-n-propyl-(6,7,8,9-tetrahydro-1H-benzo[g]indol-7yl)amine (3a, Chart 1) ($R_1R_2$ n-propyl; $R_3$ hydrogen; $R_4$ $CH_2$; YZ (a); $R_5R_6$ H)

A solution of 7-di-n-propylamino-6,7,8,9-tetrahydro-1H-benzo[g]indole-2,3-dione, 2a, (Chart 1) (22.0 g, 73.2 mmol) in dry diethyl ether (100 mL) was added dropwise to a suspension of lithiumaluminum hydride (9.0 g, 237 mmol) in dry diethyl ether (600 mL). After stirring overnight at ambient temperature, water (9.0 mL), 15% sodium hydroxide (9 mL) and water (27 mL) were consecutively added. The mixture was stirred for 20 minutes followed by filtration of inorganic material. The solution was dried (sodium sulfate), filtered and evaporated to yield 17 g of a blue off, which was purified on silica (acetone/methanol, 20:1) to yield 7.4 g (37%) of the pure material. For analytical and biological purposes, the fumarate salt (½ fum) was prepared which was recrystallized from ethanol/diethyl ether. m.p. 201°–205° C.

EXAMPLE 3

7-Di-n-propylamino-6,7,8,9-tetrahydro-1H-benzo[g]indole-3-carbaldehyde (4a, Chart 1) ($R_1$ n-propyl; $R_2$ butyl; $R_3$ hydrogen; $R_4$ $CH_2$; YZ (a); $R_5$ CHO; $R_6$ H)

A solution of di-n-propyl-(6,7,8,9-tetrahydro-1H-benzo[g]indol-7yl)amine, (3a, Chart 1)(0.90 g, 3.33 mmol) in dimethyl formamide (10 mL) was added dropwise to an ice-cooled solution of phosphorous oxychloride (1.2 ml, 0.73 g, 4.8 mmol) under an inert atmosphere. The solution was stirred for 10 minutes and was then heated to 50° C. After stirring for 3 hours, the solution was allowed to reach ambient temperature, stirred overnight and was then poured on ice. After basification, the mixture was heated to 80° C. for 10 minutes and then cooled. Extraction three times (dichloromethane), followed by drying (magnesium sulfate), filtering and evaporation several times with 99% ethanol, yielded 0.82 g (82%) of the material. This material was further purified on a silica column (dichloromethane/methanol, 3:1) to yield 0.53 g (53%) of the pure material as an oil.

EXAMPLE 4

7-Di-n-propylamino-1,3,6,7,8,9-hexahydro-1H-benzo[g]indole-2-one (5a, Chart 1) ($R_1R_2$ n-propyl; $R_3$ hydrogen; $R_4$ $CH_2$; YZ (a); $R_5$ H; $R_6$ O)

A solution of pyridiniumperbromide hydrobromide (560 mg, 1.83 mmol) in acetic acid (100 mL) was added to a solution of di-n-propyl-(6,7,8,9-tetrahydro-1H-benzo[g]indol-7-yl) amine, 3a (Chart 1) (400 mg, 1.48 mmol) in aqueous (90%) acetic acid while cooling on ice. The temperature was then slowly raised to 80° C. The progress of the reaction was followed by GC. When the reaction was complete (3 hours), the solution was cooled and evaporated to an aqueous residue, which was basified (10% sodium carbonate). This suspension was extracted 3 times (ethyl acetate). The combination of the organic phases was washed with water, dried (magnesium sulfate), filtered and evaporated to yield a residue of 390 mg (89%). This material was subjected to a silica column and eluated (methanol) to afford 170 mg of the pure material, which prior to biological testing was treated with ½ eq of fumaric acid and recrystallized from methanol. m.p. 136°–139° C.

EXAMPLE 5

25 Di-n-propyl-(1,6,7,8-tetrahydro-9-oxa-1-azacyclopenta[a]naphthylenee-7-yl )amine (3b, Chart 1) ($R_1R_2$ n-propyl; $R_3$ hydrogen; $R_4$ O; YZ (a); $R_5R_6$ H)

Step A. N-(8-Aminochroman-3-yl)-N-propylpropionamide (18a, Chart A).

To an ice-cooled solution of (chroman-3-yl)-N-propylpropionamide 5.5 g (22.3 mmol) in nitromethane (150 mL) was added a mixture of "nitrating acid" (6.2 vol % nitric acid, 80.6 vol % sulfuric acid, 13.2 vol % water) (13 mL). The solution was stirred for 2 hours at 0° C. Additional 4 ml of "nitrating acid" with the same composition as above was added, and the reaction mixture was stirred overnight. The reaction mixture was poured on ice and the product was extracted with dichloromethane. The organic layer was washed with water several times. The organic layer was separated, dried (magnesium sulfate) and the solvent was evaporated, yielding 4.55 g (70%) of a mixture of 6-nitro-3-(N-Propionyl-N-n-propylamino)chroman (17b, Chart A) and 8-nitro-3-(N-Propionyl-N-n-propylamino)-chroman (17a, Chart A). The crude mixture was dissolved in abs. ethanol (300 mL) and hydrogenated in a Parr apparatus with Pd/C. for 2.5 hours. The mixture was then filtered and the solvent evaporated, yielding a mixture of N-(6-amino- and N-(8-amino-chroman-3-yl)-N-propylpropionamide (18b and 18a respectively). The regioisomers was separated on a silica column first eluted with ether and then dichloromethane/methanol (19:1) yielding 1.1 g of 18a (17%).

Step B: N,N-Dipropyl-chroman-3,8-diamine (1b, Chart A and 1).

To a solution of N-(8-amino-chroman-3-yl)-N-propylpropionamide, 18a (Chart A) (1.1 g, 3.77 mmol) in anhydrous tetrahydrofuran was added lithiumaluminum chloride (600 mg, 15.8 mmol). The mixture was stirred for 1.5 hours at room temperature. Excess hydride was quenched by addition of water (0.6 mL), 15% sodium hydroxide (0.6 mL) and water (1.2 mL). The mixture was filtered and the solvent evaporated yielding 911 mg (98%) of 2 as an oil. The free base was converted to the dihydrochloride with a saturated hydrochloric acid solution in ethanol yielding 1.2 g of the desired compound as the di-HCl-salt.

Step C: Di-n-propylamino-1,6,7,8-tetrahydro-9-oxa-1-azacyclopenta[a]naphthylenee-2,3-dione (2b, Chart 1).

This compound was prepared in an analogous manner as for compound 2a from N,N-dipropyl-chroman-3,8-diamine dihydrochloride, 1b (Chart A and 1) (1.2 g, 3.74 mmol) in deionized water (24 mL) treating with chloral hydrate (677 mg, 4.10 mmol), hydroxylamine hydrochloride (920 mg, 13.23 mmol) and anhydrous sodium sulphate (4.4 g). After usual work-up and extraction (dichloromethane), the organic layer was dried and evaporated yielding 1.04 g (3.26 mmol) of the corresponding oxime which was treated as described for compound 2a with ice-cooled 90% sulfuric acid (165 mL). After usual work-up, 380 mg (34%) of the desired compound was afforded as a red oil. The crude product was used in the next step without purification.

Step D: Di-n-propyl-(1,6,7,8-tetrahydro-9-oxa-1-azacyclopenta[a]naphthylenee-7-yl)amine (3, Chart 1).

To a solution of di-n-propylamino-1,6,7,8-tetrahydro-9-oxa-1-azacyclopenta[a]naphthylenee-2,3-dione, 2b (Chart 1) (380 mg, 1.26 mmol) in dry ether (50 mL) was added lithiumaluminum hydride (500 mg, 13.1 mmol) in portions. The mixture was stirred for 3 hours at ambient temperature. The reaction was quenched by addition of water (0.5 mL), 15% sodium hydroxide (0.5mL) and water (1.5 mL). The mixture was filtered and the solvent evaporated yielding 197 mg of crude 5 as an oil. The product was chromatographed on silica with dichloromethane/methanol (19:1) as eluant yielding 45 mg (14%) of the desired compound. The amine was converted into its neutral fumarate with 10 mg of fumaric acid dissolved in 99% ethanol, yielding 22 mg (0.5 fumarate). m.p. 163°–165° C. (0.5 fumarate).

EXAMPLE 6

6-Di-n-propylamino-5,6,7,8-tetrahydro-1H-benzo[f]indole-2,3-dione (8, Chart 2) ($R_1R_2$ n-propyl; $R_3$ hydrogen; $R_4$ $CH_2$; XY indole; $R_5R_6$ O)

This compound was prepared from 7-amino-2-di-n-propylamino-1,2,3,4-tetrahydronaphthylenee, (6, Chart 2) in a similar manner as for compound 2a (Chart 1). This intermediate compound was prepared according to Stjernlof et al. (Eur. J. Med. Chem. 1993 Accepted for publication).

EXAMPLE 7

Di-n-propyl-(5,6,7,8-tetrahydro-1H-benzo[f]indol-6-yl)amine (11a, Chart 2) ($R_1R_2$ n-propyl; $R_3$ hydrogen; $R_4$ $CH_2$; XY indole; $R_5R_6$ H)

Step A: Di-n-propyl-(6,7,8,9-tetrahydro-3H-benzo[e]indol-7-yl)amine (9, Chart 2) ($R_1R_2$ n-propyl; $R_3$ hydrogen; $R_4$ $CH_2$; YZ (b); $R_5R_6$ H).

This compound (disclosed in EPA 0055043) was synthesized in a similar manner as compound 3a (Chart 1) from the mixture above (7a and 8a, Chart 2) yielding an isomeric mixture of 9a and 11a (Chart 2). This compound is shown here to show the preparation of Example 9, below. Purification on silica (dichloromethane/methanol, 19:1) afforded the pure isomers. m.p. 112°–114° C.

Step B: The title compound was obtained as a second isomer from foregoing step.

EXAMPLE 8

7-Di-n-propylamino-6,7,8,9-tetrahydro-3H-benzo[e]indole-1-carbaldehyde (10a, Chart 2) ($R_1R_2$ n-propyl; $R_3$ hydrogen; $R_4$ $CH_2$; YZ (b); $R_5$ H; $R_6$ CHO)

This material was prepared in the same manner as described for compound 4a (Chart 1) from di-n-propyl-(6,7,8,9-tetrahydro-3H-benzo[e]indol-7-yl)amine, 9a (Chart 2).

EXAMPLE 9

6-Di-n-propylamino-5,6,7,8-tetrahydro-1H-benzo [f] indole-3-carbaldehyde (12a, Chart 2) ($R_1R_2$ n-propyl; $R_3$ hydrogen; $R_4$ $CH_2$; XY indole; $R_5$ CHO; $R_6$ H)

This material was prepared in the same manner as described for compound 4a (Chart 1) from 7-di-n- propylamino-6,7,8,9-tetrahydro-3H-benzo[e]indole-1-carbaldehyde, 10a, (Chart 2)

EXAMPLE 10

7-Di-n-propylamino-6,7,8,9-tetrahydro-3H-benzo[e]indole-1-carbonitrile (10b, Chart 2) ($R_1R_2$ n-propyl; $R_3$ hydrogen; $R_4$ $CH_2$; XY (b); $R_5$ H; $R_6$ CN)

To an ice-cold solution of di-n-propyl-(6,7,8,9-tetrahydro-3H-benzo[e]indol-7yl)amine, 9a (Chart 2) (180 mg, 0.67 mmol) in acetonitrile (5 mL) was added dropwise with a solution of chlorosufonyl isocyanate (60 mL, 0.68 mmol) in acetonitrile (1 mL) over 10 minutes. After stirring for 1 hour, dimethyl formamide (100 mL) was added and the reaction was stirred for an additional 2 hours. Water was added and extraction (dichloromethane) followed by evaporation of the combined organic extracts afforded 170 mg (86%) of the crude product. Purification on a silica column (hexane/ethyl acetate/methanol) afforded 45 mg (23%) of the pure material.

EXAMPLE 11

7-[(1R-Phenyl-ethyl)-propyl-amino]-6,7,8,9-tetrahydro-3H-benzo[e]indole-1,2-dione 7b:2, Chart 2) ($R_1$ n-propyl; $R_2$ ethyl phenyl; $R_3$ hydrogen; $R_4$ $CH_2$; YZ (b); $R_5R_6$ O) and 6-[(1R-phenyl-ethyl)-propyl-amino]-5,6,7,8-1H-benzo[f]indole-2,3-dione (8b:2, Chart 2) ($R_1$ n-propyl; $R_2$ ethyl phenyl; $R_3$ hydrogen; $R_4$ $CH_2$; XY indole; $R_5R_6$ O)

Step A: [4-(1,3-Dioxo-1,3-dihydro-isoindol-2-yl)-phenyl]-acetic acid (19, Chart B).

Phthalic acid anhydride (15.1 g, 102 mmol) and 4-amino phenyl acetic acid (15.2 g, 102 mmol) were dissolved in acetic acid and heated at reflux for 1 hour. Upon cooling on an ice bath, the product crystallized. The solid was filtered off, washed with water, and dried under vacuum overnight. The yield of the title compound was 24.1 g (86%) as an off white solid.

$^1$H NMR (300 MHz, acetone-$d_6$) d 3.75 (s, 2H), 7.52 (sb, 4H), 7.95 (m, 4H).

Step B: [4-(1,3-Dioxo-1,3-dihydro-isoindol-2-yl)-phenyl]-acetylchloride (20, Chart B).

A slurry of [4-(1,3-dioxo-1,3-dihydro-isoindol-2-yl)-phenyl]-acetic acid (19, Chart B) (24.0 g, 85.4 mmol) in dichloromethane (300 ml) was treated with thionyl chloride (12.4 ml, 170 mmol). After heating at reflux temperature for 3.5 hours, the solvent and excess reagent were removed by evaporation to yield sufficiently pure product (25.4 g, 99%).

$^1$H NMR (300 MHz, $CDCl_3$) d 4.22 (s, 2H), 7.48 (m, 4H), 7.82 (m, 2H), 7.98 (m, 2H).

Step C:2-(6-Oxo-5,6,7,8-tetrahydro-naphthylenee-2-yl)-isoindole-1,3-dione (21, Chart B).

A slurry of [4-(1,3-dioxo-1,3-dihydro-isoindol-2yl)-phenyl]-acetyl chloride (20, Chart B) 25.4 g (85.4 mmol) in dichloromethane (380 ml) was cooled on an ice bath. To the stirred slurry was added aluminum chloride 23.7 g (178 mmol) and ethene gas was bubbled through the mixture for 5 hours. Then the contents of the reaction flask were poured into a mixture of water (100 ml), crushed ice (100 g) and solid sodium carbonate (20 g). Acetic acid (50 ml) was added and the dichloromethane phase separated. The aqueous layer was extracted with the same solvent. The combined extracts were washed with water, saturated sodium hydrogen carbonate and brine. After drying over magnesium sulfate, the solvent was removed yielding 23.7 g (95%) of an off white solid. The purity was >97% (GC).

$^1$H NMR (300 MHz, $CDCl_3$) d 2.57 (t, 2H), 3.12 (t, 2H), 3.62 (s, 2H), 7.30 (m, 3H), 7.80 (m, 2H), 7.95 (m, 2H);

$^{13}$C NMR (75.4 MHz, $CDCl_3$) d 28.4, 37.8, 44.8, 123.9, 125.3, 125.9, 129.0, 130.2, 131.7, 133.6, 134.5, 137.7, 167.4, 209.8; MS (EI) m/e 291 (M+, 100), 249 (91), 115 (68), 76 (61), 104 (37), 117 (33), 263 (28), 77 (20).

Step D: 2-[6-(1R-Phenyl-ethylamino)-5,6,7,8-tetrahydro-naphthylenee-2-yl]-isoindole-1,3-dione (22, Chart B).

A stirred solution of 2-(6-oxo-5,6,7,8-tetrahydro-naphthylenee-2-yl)-isoindole-1,3-dione, 21 (Chart B) (19.8 g, 68 mmol) and R -(+)-a-methyl benzyl amine (8.50 g, 70 mmol) in 1,2-dichloroethane (350 ml) was treated with acetic acid (5 ml) and portionwise additions of sodium triacetoxyborohydride (16.0 g, 75 mmol). After stirring at ambient temperature for 6 hours. the reaction mixture was quenched with saturated sodium carbonate. The organic layer was separated and the aqueous layer extracted with 1,2-dichloroethane and diethyl ether. The combined organic extracts were dried over magnesium sulfate and the solvents removed. To the residue was added ethanol (200 ml) followed by HCl saturated ethanol. The precipitate was filtered and washed with ethanol and diethyl ether. Drying under vacuum yielded 20.0 g of the HCl salt. An additional 1.8 g was recovered from the mother liquor, giving a total of 21.8 g. (The diasteromer at compound 22 (Chart B) leads to the synthesis of compound 9a:1 and 9a:2, Chart 2.)

(74%) as a mixture of diastereomers. The GC/MS data below refers to analysis of the diastereomeric mixture of the free bases. MS (EI) of the less retained diastereomer: m/e 396 (M+, 4), 105 (100), 288 (31), 79 (24), 77 (23), 130 (22), 392 (22), 277 (18) of the more retained diastereomer: 396 (M+, 2), 105 (100), 288 (32), 392 (22), 77 (22), 76 (20), 104 (20), 130 (19).

Step E: N-[6-(1,3-Dioxo-1,3-dihydro-isoindol-2-yl)-1,2,3,4-tetrahydro-naphthylenee-2-yl]-N-( 1R-phenyl-ethyl)-propionamide (23:1 and 23:2, Chart B).

To a stirred slurry of 2-[6-(1R-phenyl-ethylamino)-5,6,7,8-tetrahydro-naphthylenee-2-yl]-isoindole-1,3-dione hydrochloride, 22 (Chart B) (17.3 g, 40 mmol) in dichloromethane (250 ml) was added triethyl amine (11.7 ml, 84 mmol) and propionyl chloride (4.90 ml, 56 mmol). The resulting mixture was stirred at ambient temperature for 1 hour and then quenched by addition of 10% sodium carbonate (75 ml) followed by stirring for 0.5 hour. The dichloromethane layer was then separated, washed with 10% sodium dihydrogen phosphate, water and then dried over magnesium sulfate. Removal of the solvent yielded 17.1 g (95%) of the product as a yellowish foam. The diastereomeric mixture was then separated using a preparative HPLC column (straight phase $SiO_2$), eluting with ethyl acetate/hexane 30/70. The yield of the first eluted isomer (22:1) was 7.28 g and of the later eluted (22:2) 7.85 g, both as yellowish foams. The isomeric purities of these materials as determined on an analytical HPLC column were 99% and 98% respectively. (Diastereomer 23:1 leads to the synthesis of compound 9a:1, Chart 2, and 23:2 leads to the synthesis of compound 9a:2, Chart 2.)

(23:1):
$^{13}$C NMR (75.4 MHz, $CDCl_3$) d 9.6, 17.7, 26.7, 28.3, 29.7, 33.0, 52.7, 54.8, 123.6, 123.8, 126.5, 127.0, 127.6, 128.4, 128.9, 129.5, 131.7, 134.2, 137.0, 137.3, 140.1, 167.3, 173.3.

(23:2):
$^{13}$C NMR (75.4 MHz, $CDCl_3$) d 9.6, 17.8, 27.5, 28.5, 29.7, 31.8, 52.6, 54.6, 123.6, 123.8, 126.4, 126.9, 127.6, 128.5, 128.8, 129.5, 131.7, 134.2, 137.1, 140.1, 167.3, 173.4.

Step F: N-(6-Amino-1,2,3,4-tetrahydro-naphthylenee-2-yl)-N-(1R-phenyl-ethyl)-propionamide (24:2, Chart B).

A solution of N-[6-(1,3-dioxo-1,3-dihydro-isoindol-2-yl)-1,2,3,4-tetrahydro-naphthylenee-2-yl]-N-(1R-phenyl-ethyl)-propionamide, 23:2 ( Chart B ) (7.0 g, 15.5 mmol) was dissolved in 300 ml ethanol. This solution was treated with hydrazine hydrate (0.85 ml, 17 mmol) and heated to 50° C. for 1 hour. The solvent and excess reagent were then removed by evaporation under vacuum. The residue was taken up in 1% hydrochloric acid (200 ml). This solution was filtered through a celite pad, basified (sodium carbonate) and extracted with dichloromethane. Additional material was recovered from the celite by extraction with dichloromethane. The latter extract was washed with a sodium carbonate solution and combined with the former. Drying over magnesium sulfate and removal of the solvent yielded 5.39 g (106%) as an brownish oil which was >96% pure by GC. (Diastereomer 24:2 leads to the synthesis of compound 9a:2, Chart 2.)

$^{13}$C NMR (75.4 MHz, CDCl$_3$) d 9.7, 18.1, 27.9, 28.6, 29.9, 31.1, 53.0, 54.1, 113.2, 114.7, 126.8, 127.4, 128.1, 128.4, 129.6, 136.7; 140.4, 143.7, 173.6; MS (EI) m/e 322 (M+, 0.2), 145 (100), 144 (24), 146 (13), 105 (10), 130 (8), 77 (5).

Step G: N-(6-Amino-1,2,3,4-tetrahydro-naphthylenee-2-yl)-N-(1R-phenyl-ethyl)-propionamide (24:1, Chart B).

This compound was prepared from 23:1 as described for 24:2 above. (Diastereomer 24:1 leads to the synthesis of compound 9a:1, Chart 2.)

$^{13}$C NMR (75.4 MHz, CDCl$_3$) d 9.7, 18.1, 27.2, 28.6, 29.9, 32.4, 53.4, 54.7, 113.2, 114.8, 126.6, 127.1, 127.5, 128.4, 129.7, 137.2, 140.6, 144.1, 173.4; MS (EI) m/e 322 (M+, 0.1), 145 (100), 144 (25), 146 (13), 130 (9), 105 (8), 119 (5), 77 (3).

Step H: N-2-(1R-Phenyl-ethyl)-N-2-propyl-1,2,3,4-tetrahydro-naphthylenee-2,6-diamine (6b:2, Chart B and 2).

To a stirred slurry of lithium aluminum hydride (2.5 g, 66 mmol) in dry tetrahydrofuran (THF) (300 ml) was added dropwise a solution of N-(6-amino-1,2,3,4-tetrahydro-naphthylenee-2-yl)-N-(1R-phenyl-ethyl)-propionamide, 24:2 (Chart B) (5.0 g, 15.5 mmol) in THF (100 ml). The mixture was stirred overnight at ambient temperature and then quenched by the consecutive addition of water (2.5 ml), 15% sodium hydroxide (2.5 ml) and water (15 ml). The solution was filtered through a celite pad and the solvent removed, yielding 4.96 (104%) of a brownish oil, which was used in the following step without further purification.

$^{1}$H NMR (300 MHz, CDCl$_3$) d 0.85 (t, 3H), 1.40 (d, 3H), 1.45 (m, 2H), 1.68 (m, 1H), 1.95 (m, 1H), 2.50–2.85 (m, 6H), 2.95 (m, 1H), 3.22 (sb, 2H), 4.08 (q, 1H), 6.38 (d, 1H), 6.45 (dd, 1H), 6.81 (d, 1H), 7.15–7.50 (m, 5H); $^{13}$C NMR (75.4 MHz, CDCl$_3$) d 11.9, 17.9, 24.0, 27.8, 30.2, 33.0, 47.8, 54.5, 57.5, 113.2, 114.8, 126.3, 127.2, 127.6, 128.0, 130.1, 137.3, 143.9, 145.7; MS (EI) m/e 308 (M+, 21), 146 (100), 105 (77), 119 (44), 145 (39), 188 (30), 175 (29), 144 (29), 203 (25), 130 (22).

Step I: N-2-(1R-Phenyl-ethyl)-N-2-propyl-1,2,3,4-tetrahydro-naphthylenee-2,6-diamine (6b:1, Chart B and 2).

This compound was prepared from 23:1 as described for 6b:2 above.

$^{1}$H NMR (300 MHz, CDCl$_3$) d 0.80 (t, 3H), 1.40 (d, 3H), 1.50 (m, 3H), 1.68 (m, 1H), 2.40–2.75 (m, 6H), 2.95 (m, 1H), 3.33 (sb, 2H,), 3.98 (q, 1H), 6.32 (s, 1H), 6.42 (d, 1H), 6.83 (d, 1H), 7.15 (m, 1H), 7.25 (m, 2H), 7.37 (d, 2H); $^{13}$C NMR (75.4 MHz, CDCl$_3$) d 11.8, 19.4, 24.2, 26.9, 30.1, 33.4, 48.2, 54.7, 58.3, 113.2, 112.8, 126.4, 127.0, 127.5, 128.0, 130.1, 137.3, 144.0, 145.9; MS (EI) m/e 308 (M+, 30), 146 (100), 105 (81), 119 (55), 145 (44), 175 (39), 188 (36), 203 (35), 144 (30), 130 (26).

Step J: 7-[(1R-Phenyl-ethyl)-propyl-amino]-6,7,8,9-tetrahydro-3H-benzo[e]indole-1,2-dione (7b:2, Chart 2) and 6-[(1R-phenyl-ethyl)-propyl-amino]-5,6,7,8-1H-benzo[f]indole-2,3-dione (8b:2, Chart 2).

A mixture of N-2-(1R-phenyl-ethyl)-N-2-propyl-1,2,3,4-tetrahydro-naphthylenee-2,6-diamine as its dihydrochloride, 6b:2 (Chart B and 2) (6.13 g, 16.1 mmol), chloral hydrate (2.92 g, 17.7 mmol), hydroxylamine hydrochloride (3.54 g, 50.9 mmol) and anhydrous sodium sulfate (17.99 g) was heated at reflux temperature under a nitrogen atmosphere in water (67 ml) for 1 hour. After cooling to room temperature, the mixture was basified with a 10% ammonium hydroxide solution (110 ml). The aqueous layer was then extracted with several portions of ethyl acetate. The solvent was removed and the resulting brown oil (5.5 g) was treated with ice cold 90% sulfuric acid (100 ml). This mixture was stirred at −30° C. for 1 hour, then gradually warmed to 80° C. where it was kept for 0.5 hour. The heat was then removed and the stirring continued for 1 hr. at room temperature. The contents of the reaction flask were then poured on ice (1000 g), the pH adjusted to 8–9 with konc. ammonium hydroxide followed by extraction of the basic aqueous solution with several portions of ethyl acetate. Drying over magnesium sulfate and removal of the solvent yielded 3.80 g (65%) of a red oil. $^{1}$H NMR analysis of this crude material revealed the regioisomeric composition (7b:2) to (8b:2) to be approximately 4:1. This material was used in the subsequent step without any attempt to separate the isomers.

Stereoisomers of EXAMPLE 11: 7-[(1R-Phenyl-ethyl)-propyl-amino]-6,7,8,9-tetrahydro-3H-benzo[e]indole-1,2-dione (7b:1, Chart 2) and 6-[(1R-phenyl-ethyl)-propyl-amino]-5,6,7,8-1H-benzo[f]indole-2,3-dione (8b:1,Chart 2).

The synthesis of the mixture of the title compounds was conducted in accordance with the above procedure 6b:1, yielding a mixture of regioisomeres in similar proportions.

EXAMPLE 12

(1R-Phenyl-ethyl)-propyl-(6,7,8,9-tetrahydro-3H-benzo[e]indol-7-yl)-amine (9b:2, Chart 2) (R$_1$ n-propyl; R$_2$ ethyl phenyl; R$_3$ hydrogen; R$_4$ CH$_2$; YZ (b); R$_5$R$_6$ H)

To a stirred suspension of lithium aluminum hydride (3.0 g, 79 mmol) in dry diethyl ether (200 ml) was added dropwise a solution of a 4:1 mixture of 7-[(1R-phenyl-ethyl)-propyl-amino]-6,7,8,9-tetrahydro-3H-benzo[e]indole-1,2-dione, 7b:2 (Chart 2) and 6-[(1R-phenyl-ethyl)-propyl-amino]-5,6,7,8-1H-benzo[f]indole-2,3-dione, 8b:2 (Chart 2) (3.8 g, 10.5 mmol) in a 1:1 tetrahydrofuran/diethyl ether mixture (100 ml). After the addition was completed stirring at ambient temperature was continued for 2 hours. Workup as described for (6b:2, Chart B and 2) yielded 3.2 g of a blue off which was chromatographed on a silica column. The yield of the pure title compound, as an oil was 0.66 g (24% based on the content of (7b:2) in the starting material).

$^{1}$H NMR (300 MHz, CDCl$_3$) d 0.83 (t, 3H), 1.42 (d, 3H), 1.50 (m, 2H), 1.85 (m, 1H), 2.10 (m, 1H), 2.45–3.10 (m, 7H), 4.10 (q, 1H), 6.42 (m, 1H), 6.83 (d, 1H), 7.10–7.35 (m, 6H), 7.42 (d, 2H), 7.95 (sb, 1H); $^{13}$C NMR (75.4 MHz, CDCl$_3$) d 11.8, 18.0, 24.0, 27.1, 27.5, 33.7, 47.8, 54.7, 57.5, 100.4, 108.6, 123.4, 123.9, 126.2, 126.8, 127.5, 127.6, 127.7, 127.9, 133.5, 146.1; MS (EI) m/e 332 (M+, 18), 170 (100), 105 (75), 143 (61), 169 (48), 168 (44), 188 (39), 199 (32), 154 (23), 227 (23), 155 (18), 303 (15).

Stereoisomer of Example 12: (1R-Phenyl-ethyl)-propyl-(6,7,8,9-tetrahydro-3H-benzo[e]indol-7-yl)-amine (9b:1, Chart 2).

Treatment of a mixture of 7b:1 and 8b:1 as described for the preparation of 9b:2 above yielded the title compound.

$^{1}$H NMR (300 MHz, CDCl$_3$) d 0.86 (t, 3H), 1.45 (d, 3H), 1.50 (m, 2H), 1.68 (m, 1H), 1.85 (m, 1H), 2.58 (m, 2H), 2.70–3.20 (m, 5H), 4.10 (q, 1H), 6.45 (m, 1H), 6.92 (d, 1H), 7.10–7.32 (m, 6H), 7.42 (m, 2H), 8.08 (sb, 1H); MS (EI) m/e 332 (M+, 20), 170 (100), 105 (65), 143 (46), 199

(38), 169 (37), 188 (37), 168 (36), 227 (27), 162 (20), 154 (17), 303 (17).

EXAMPLE 13

(+)-7-Dipropylamino-6,7,8,9-tetrahydro-3H-benzo[e]indole-1-carbaldehyde (10a:2, Chart 2) ($R_1R_2$ n-propyl; $R_3$ hydrogen; $R_4$ $CH_2$; YZ (b); $R_5$ H; $R_6$ CHO)

Step:A (+)-Propyl-(6,7,8,9-tetrahydro-3H-benzo[e]indol-7-yl)-amine (9e:2, Chart 2)—Not a compound of the subject invention—($R_1$ H; $R_2$ n-propyl; $R_3$ hydrogen; $R_4$ $CH_2$; YZ (b); $R_5R_6$ H).

To a stirred solution of (1R-phenyl-ethyl)-propyl-(6,7,8,9-tetrahydro-3H-benzo[e]indol-7-yl)-amine, 9b:2 (Chart 2) (0.60 g, 1.8 mmol) in ethanol was added 0.4 g 10% palladium on carbon and 1.0 g ammonium formate. The mixture was stirred at ambient temperature for 1.5 hours. and then filtered through a celite pad. The solvent was removed and to the residue was added 10% sodium carbonate solution and ethyl acetate. The organic layer was separated and the aqueous layer was extracted with ethyl acetate. Drying of the combined extracts over magnesium sulfate and removal of the solvent yielded 0.39 g (89%) of the title compound as a colorless oil. This procedure is shown to provide pathway to Example 17.

$^1$H NMR (300 MHz, $CDCl_3$) d 0.95 (t, 3H), 1.57 (q, 2H), 1.72 (m, 1H), 2.20 (m, 1H), 2.73 (m, 3H), 2.90–3.22 (m, 4H), 6.50 (m, 1H), 6.94 (d, 1H), 7.17 (m, 2H), 8.48 (sb, 1H); $^{13}$C NMR (75.4 MHz, $CDCl_3$) d 11.9, 23.5, 25.4, 29.5, 36.6, 49.0, 54.0, 100.3, 108.9, 123.6, 123.9, 125.6, 126.9, 127.6, 133.8; MS (EI) m/e 228 (M+, 30), 143 (100), 168 (46), 169 (42), 170 (34), 144 (22), 154 (19), 115 (15), 167 (15), 199 (12), 155 (10), 197 (7); $[a]_D^{20}$+77.7° (c=1.0, MeOH).

Stereoisomer of STEP A: (−)-Propyl-(6,7,8,9-tetrahydro-3H-benzo[e]indol-7-yl)-amine. (9e:1, Chart 2).

This compound was prepared as described for 9b:1 as described for 9e:2 above.

$^1$H NMR (300 MHz, $CDCl_3$) d 0.95 (t, 3H), 1.60 (q, 2H), 1.75 (m, 1H), 2.22 (m, 1H ), 2.77 (m, 3H), 2.90–3.22 (m, 4H), 6.50 (m, 1H), 6.92 (d, 1H), 7.17 (m, 2H), 8.48 (sb, 1H); $^{13}$C NMR (75.4 MHz, $CDCl_3$) d 11.9, 23.3, 25.3, 29.2, 36.3, 48.9, 54.0, 100.3, 109.0, 123.7, 123.8, 125.3, 126.9, 127.5, 133.8; MS (EI) m/e 228 (M+, 45), 143 (100), 168 (50), 169 (45), 170 (37), 144 (21), 154 (19), 199 (16), 115 (16), 167 (15), 197 (13).

Step B: (+)-Dipropyl-(6,7,8,9-tetrahydro-benzo[e]indol-7-yl)-amine (9a:2, Chart 2)—Not a compound of the subject invention—($R_1R_2$ n-propyl; $R_3$ hydrogen; $R_4$ $CH_2$; YZ (b); $R_5R_6$ H).

To a stirred solution of (+)-propyl-(6,7,8,9-tetrahydro-3H-benzo[e]indol-7-yl)-amine, 9e:2 (Chart 2) (0.35 g, 1.53 mmol) in 1,2-dichloroethane (20 ml) was added sodium triacetoxy borohydride (0.39 g, 1.83 mmol), propionaldehyde (0.20 ml, 2.8 mmol) and two drops of acetic acid. The solution was stirred at ambient temperature for 2 hours. Then the solvent was removed, the residue taken up in water and basified (10% sodium hydroxide). The liberated amine was extracted with several portions of diethyl ether, dried over magnesium sulfate and the solvent removed to yield an oil. The oil was chromatographed on a silica column, eluting with methanol, yielding 0.35 g (85%) of an off white solid.

$^1$H NMR (300 MHz, $CDCl_3$) d 0.90 (t, 6H), 1.50 (m, 4H), 1.73 (m, 1H), 2.14 (m, 1H), 2.55 (m, 4H), 2.80-3.15 (m, 4H), 8.20 (dd, 1H), 6.49 (m, 1H), 6.87 (d, 1H), 7.17 (m, 2H), 8.17 (sb, 1H); $^{13}$C NMR (75.4 MHz, $CDCl_3$) d 11.9, 22.2, 25.8, 27.1, 31.8, 52.7, 57.2, 100.5, 108.7, 128.5, 124.1, 126.9, 127.0, 127.8, 133.6; MS (EI) m/e 270 (M+, 9), 170 (100), 143 (47), 168 (30), 169 (26), 241 (24), 154 (19), 171 (14), 155 (14), 144 (14), 115 (10); $[a]_D^{20}$+64.7° (c=1.0, MeOH).

Stereoisomer of STEP B: (−)-Dipropyl-(6,7,8,9-tetrahydro-benzo[e]indol-7-yl)-amine (9a:1, Chart 2).

This compound was prepared from 9e:1 as described for 9a:2 above.

$^1$H NMR (300 MHz, $CDCl_3$) d 0.91 (t, 6H), 1.52 (m, 4H), 1.72 (m, 1H), 2.15 (m, 1H), 2.55 (m, 4H), 2.80–3.15 (m, 4H), 2.22 (dd, 1H), 6.51 (m, 1H), 6.88 (d, 1H), 7.18 (m, 2H), 8.20 (sb, 1H); $^{13}$C NMR (75.4 MHz, $CDCl_3$) d 12.0, 22.2, 25.9, 27.1, 31.8, 52.7, 57.2, 100.5, 108.7, 123.5, 124.1, 126.9, 127.0, 127.8, 133.6; MS (EI)m/e 270 (M+, 17), 170 (100), 143 (42), 241 (33), 168 (21), 154 (14), 171 (14), 144 (12), 155 (12), 167 (9), 115 (8); $[a]_D^{20}$−62.9° (c=0.17, MeOH).

Step C: (+)-7-Dipropylamino-6,7,8,9-3H-benzo[e]indole-1-carbaldehyde (10a:2, Chart 2) ($R_1R_2$ n-propyl; $R_3$ hydrogen; $R_4$ $CH_2$; YZ (b); $R_5$ H; $R_6$ CHO).

This compound was synthesized from 9a:2 according to the procedure given for compound 4a (Chart 1).

$^1$H NMR (300 MHz, $CDCl_3$) d 0.89 (t, 6H), 1.50 (m, 4H), 1.68 (m, 1H), 2.18 (m, 1H), 2.55 (m, 4H), 2.80–3.10 (m, 3H), 3.20 (m, 1H), 3.60 (m, 1H), 7.02 (d, 1H), 7.19 (d, 1H), 7.89 (s, 1H), 9.97 (sb, 1H), 10.12 (s, 1H); $^{13}$C NMR (75.4 MHz, $CDCl_3$) d 11.7, 21.6, 25.5, 29.9, 32.8, 52.4, 56.4, 109.5, 120.7, 123.6, 125.9, 129.8, 130.7, 134.7, 135.3, 185.4; MS (EI) m/e 298 (M+, 42), 199 (100), 198 (97), 269 (79), 170 (50), 100 (24). $[a]_D^{20}$+59.4° (c=1.0, MeOH).

EXAMPLE 14 cis-7-Dipropylamino-6-methyl-6,7,8,9-tetrahydro-3H-benzo[e]-indole-1,2-dione ($R_1R_2$ n-propyl; $R_3$ $CH_3$; $R_4$ $CH_2$; YZ (b); $R_5R_6$ O) and cis-6-dipropylamino-5-Methyl-5,6,7,8-tetrahydro-1H-benzo[f]indole-2,3-dione (7d and 8d Chart 2) ($R_1R_2$ n-propyl; $R_3$ $CH_3$; $R_4$ $CH_2$; $X_1Y$ indole; $R_5R_6$ O)

Step A: 4-Bromo-phenyl acetic acid chloride (25, Chart C).

To a stirred solution of 4-bromo-phenyl acetic acid (25 g, 116 mmol) in dichloromethane (250 ml) was added thionyl chloride (13 ml, 170 mmol). The mixture was heated under reflux for 24 hours and then the solvent and the excess reagent were removed. The residue was distilled under reduced pressure (110° C./2 mmHg) to yield 19.8 g (73%) of the title compound.

$^1$H NMR (300 MHz, $CDCl_3$) d 4.08 (s, 2H), 7.12 (d, 2H), 7.49 (d, 2H).

Step B: 6-Bromo-3,4-dihydro-2(1H)-naphthyleneone (26, Chart C).

A solution of 4-bromo-phenyl acetic acid chloride, 25 (Chart C) (19.8, 85 mmol) in dichloromethane was cooled on an ice bath. Then the stirred solution was saturated with ethene gas and aluminum trichloride (22.0 g, 165 mmol) was added in portions. The bubbling of ethene was continued for 5 hours. The mixture was then poured into and ice 10% hydrochloric acid mixture and the organic layer separated. The aqueous layer was extracted with dichloromethane and the combined extracts were dried over magnesium sulfate. The solvent was removed and the residue lixiviated with hexane and the solid filtered off. The hexane was placed in the cold store to precipitate a second crop of solid. The yield of sufficiently pure (>96% by GC) product was 11.0 g (58%) as an off white solid.

¹H NMR (300 MHz, CDCl₃) d 2.55 (t, 2H), 3.05 (t, 2H), 3.51 (s, 2H), 7.00 (d, 1H), 7.36 (d, 1H), 7.39 (s, 1H); MS (EI) m/e 326/324 (M+, 61/59), 182 (100), 184 (95) 115 (48), 103 (41), 117 (37), 116 (26), 77 (20).

Step C: 6-Bromo-1-methyl-3,4-dihydro-1H-naphthylenee-2-one (27, Chart C).

A solution of 6-bromo-3,4-dihydro-2(1H)-naphthyleneone, 26 (Chart C) (3.83 g, 17.0 mmol) and pyrrolidine (2.2 ml, 26 mmol) in benzene (75 ml) was heated at reflux for 2 hours, (when the formation of the enamine was judged completed by GC). The benzene and the excess pyrrolidine were removed and the residue redissolved in dioxane (25 ml). To the dioxane solution was then added methyl iodide (8.0 ml, 128 mmol) and the mixture was heated at reflux temperature for 18 hours. To this mixture was then added 5% acetic acid (25 ml) and the heating was continued for 4 hours, followed by evaporation of the solvents under vacuum (1 mmHg). The residue was taken up in diethyl ether, washed with water and dried over magnesium sulfate. To this solution was added a small amount of (2,6-ditert.butyl-4-methyl phenol [BHT]) to prevent autooxidation. Evaporation of the solvent yielded 4.1 g (100%) of an oil which was 85% pure by GC analysis, the remainder being unreacted starting material.

This was used in the subsequent step without further purification.

¹H NMR (300 MHz, CDCl₃) d 1.45 (d, 3H), 2.40–2.60 (m, 2H), 2.95–3.15 (m, 2H), 3.45 (q, 1H), 7.07 (d, 1H), 7.38 (m, 2H); MS (EI) m/e 240/238 (M+, 23/24), 116 (100), 115 (88), 117 (56), 196 (54), 198 (54), 197 (26), 195 (22), 91 (21).

Step D: cis-(6-Bromo-1-methyl-6,7,8,9-tetrahydro-naphthylenee-2-yl)-propylamine (28, Chart C).

To a stirred solution of 6-bromo-1-methyl-3,4-dihydro-1H-naphthylenee-2-one, 27 (Chart C) (4.1 g, 17 mmol), propylamine (1.5 ml, 18 mmol) and 0.5 g BHT in tetrahydrofuran (THF) (50 ml) was added portionwise sodium triacetoxyborohydride (4.5 g, 21 mmol). The mixture was stirred overnight, rigorously protected from atmospheric oxygen. Then was 10% hydrochloric acid (50 ml) added and most of the THF removed. The residual aqueous layer was washed with diethyl ether, basified and extracted with ether. Drying over magnesium sulfate yielded 2.4 g of an oil which was purified by chromatography on a silica column. The yield of the title compound as a colorless oil was 1.56 g (38% based on the content of (27) in the starting material).

¹H NMR (300 MHz, CDCl₃) d 0.94 (t, 3H), 1.12 (d, 3H), 1.53 (m, 2H), 1.74 (m, 2H), 2.61 (m, 2H), 2.81 (m, 2H), 2.90 (m, 1H), 3.02 (m, 1H), 6.97 (d, 1H), 7.20 (m, 2H); MS (EI) m/e 283/281 (M+, 39/40), 144 (100), 115 (96), 128 (92), 254 (85), 252 (85), 117 (83), 223 (78), 225 (76).

Step E: cis-(6-Bromo-1-methyl-6,7,8,9-tetrahydro-naphthylenee-2-yl)-dipropylamine (29, Chart C).

To stirred solution of cis-(6-bromo-1-methyl-6,7,8,9-tetrahydro-naphthylenee-2-yl)-propylamine, 28 (Chart C) (1.56 g, 5.55 mmol), propionaldehyde (0.78 g, 13 mmol) and BHT (0.20 g) in THF was added portionwise sodium triacetoxyborohydride (3.0 g, 14 mmol). The mixture was stirred at ambient temperature for 2 hours and then the solvent was removed. The residue was dissolved in 10% hydrochloric acid (50 ml), the solution washed with diethyl ether and basified with 15% sodium hydroxide. Extraction with diethyl ether, drying over magnesium sulfate and removal of the solvent yielded 1.55 g (91%) of product as a colorless oil. The purity as determined by GC was >98%, the remainder being BHT.

¹H NMR (300 MHz, CDCl₃) d 0.88 (t, 6H), 1.18 (d, 3H), 1.46 (m, 4H), 1.77 (m, 1H), 1.91 (m, 1H), 2.56 (m, 4H), 2.75–2.95 (m, 3H), 3.05 (m, 1H), 6.97 (d, 1H), (d, 1H), 7.22 (m, 2H); ¹³C NMR (75.4 MHz,) d 11.9, 18.1, 20.8, 20.9, 29.6, 36.6, 52.8, 59.4, 119.2, 128.7, 131.0, 131.2, 137.9, 141.9; MS (EI) m/e 325/323 (M+, 14/15), 294 (100), 296 (98), 144 (97), 223 (75), 225 (73), 143 (25).

Step F: cis-6-Dipropylamino-5-methyl-5,6,7,8-tetrahydro-naphthylenee-2-carboxylic acid methyl ester (30, Chart C).

A mixture of cis-(6-bromo-1-methyl-6,7,8,9-tetrahydro-naphthylenee-2-yl)-dipropylamine, 29 (Chart C) (1.55 g, 4.78 mmol), triethylamine (1.06 g, 10.5 mmol) and methanol (10 ml) in dimethyl sulfoxide (DMSO) (15 ml) was stirred at ambient temperature for 20 minutes. Then palladium acetate (0.107 g, 0.48 mmol) and 1,3-bis-(diphenylphosphino)propane (0.196 g, 0.478 mmol) was added and carbon monoxide (CO) passed through the solution. The mixture was kept under an atmosphere of CO and heated at 80° C. for 2 hours when more triethylamine (1.06 g, 10.5 mmol) and methanol (5 ml) were added. After 6.5 hours the reaction was judged complete and the mixture allowed to cool to room temperature. The DMSO was removed by evaporation under vacuum and the residue treated with 10% sodium carbonate. The aqueous layer was extracted with several portions of diethyl ether, the combined extracts washed with water followed by drying over magnesium sulfate. Removal of the solvent yielded 1.24 g (86%) of product as an yellow oil. This material was used without further purification.

¹H NMR (300 MHz, CDCl₃) d 0.86.t (6), 1.17 (d, 3H), 1.45 (m, 4H), 1.78 (m, 1H), 1.94 (m, 1H), 2.55 (m, 4H), 2.75–3.00 (m, 3H), 3.12 (m, 1H), 3.88 (3, s), 7.16 (d, 1H), 7.77 (m, 2H); ¹³C NMR (75.4 MHz, CDCl₃) d 11.9, 17.9, 20.7, 21.0, 29.6, 37.2, 51.9, 52.8, 59.2, 126.6, 127.5, 129.4, 129.9, 135.7, 148.5, 167.3; MS (EI) m/e 303 (M+, 13), 274 (100), 203 (82), 126 (55), 128 (52), 115 (45), 171 (43), 129 (42), 98 (27), 200 (27), 143 (26).

Step G: cis-5-Methyl-N-,N-dipropyl-5,6,7,8-tetrahydro-naphthylenee-2,6-diamine (6d, Chart C and 2).

To a stirred solution of cis-6-dipropylamino-5-methyl-5,6,7,8-tetrahydro-naphthylenee-2-carboxylic acid methyl ester, 30 (Chart C) (1.20 g, 3.96 mmol) in dichloromethane (60 ml) was added concentrated sulfuric acid (25 ml) followed by the portionwise addition of sodium azide (3.50 g, 53.8 mmol) (caution, foaming). The mixture was then heated at reflux temperature overnight. After cooling the mixture was basified with 15% sodium hydroxide and the organic layer separated. The aqueous phase was extracted with dichloromethane. The combined extracts were dried over magnesium sulfate and the solvent removed to yield 1.02 g (99%) as a light brown oil. The purity according to GC analysis was >95%.

¹H NMR (300 MHz, CDCl₃) d 0.85 (t, 6H), 1.22 (d, 3H), 1.45 (m, 4H), 1.75 (m, 1H), 1.83 (m, 1H), 2.55 (m, 4H), 2.76 (m, 2H), 2.86 (m, 1H), 3.02 (m, 1H), 3.48 (sb, 2H), 6.62 (d, 1H), 6.52 (dd, 1H), 6.88 (d, 1H); ¹³C NMR (75.4 MHz, CDCl₃) d 11.9, 18.5, 20.8, 21.2, 30.0, 36.1, 52.8, 59.9, 113.5, 114.6, 130.3, 133.3, 136.4, 144.1; MS (EI) m/e 260 (M+, 6), 133 (100), 160 (64), 144 (14), 130 (13), 231 (13), 161 (8), 117 (7).

Step H: cis-7-Dipropylamino-6-methyl-6,7,8,9-tetrahydro-3H-benzo[e]-indole-1,2-dione, and cis-6-dipropylamino-5-Methyl-5,6,7,8-tetrahydro-1H -benzo[f]indole-2,3-dione (7d and 8d Chart 2).

The regioisomeric mixture of these compounds was prepared as described for the mixture of 7b:2 and 8b:2. Here the composition of 7d to 8d as determined by ¹HNMR was approximately 6:1. This mixture was used in the subsequent step without any attempt to separate the regioisomeres.

EXAMPLE 15 cis-(6-Methyl-6,7,8,9-tetrahydro-3H-benzo[e]-indol-7-yl)-dipropylamine (9d, Chart 2) ($R_1R_2$ n-propyl; $R_3$ $CH_3$; $R_4$ $CH_2$; YZ (b); $R_5R_6$ H), and cis-(5-methyl-5,6,7,8-tetrahydro-1H-benzo[f]-indol-6-yl)-dipropylamine ($R_1R_2$ n-propyl; $R_3CH_3$; $R_4$ $CH_2$; XY indole; $R_5R_6$ H)

This product was prepared using the same procedure as described for (9b:2). Here a 6:1 mixture of cis-7-dipropylamino-6-methyl-6,7,8,9-tetrahydro-3H-benzo[e]-indole-1,2-dione and cis-6-dipropylamino-5-methyl-5,6,7,8-tetrahydro-1H-benzo[f]indole-2,3-dione, 7d and 8d (Chart 2) (1.1 g, 35 mmol) was used, yielding 0.25 g of the pure title compound after chromatography of the crude product.

$^1$H NMR (300 MHz, $CDCl_3$) d 0.98 (t, 6H), 1.32 (d, 3H), 1.58 (m, 4H), 2.02 (m, 1H), 2.10 (m, 1H), 2.71 (m, 4H), 2.98–3.15 (m, 2H), 3.20–3.35 (m, 2H), 6.56 (m, 1H), 7.04 (d, 1H), 7.17 (t, 1H), 7.22 (d, 1H), 8.30 (sb, 1H); $^{13}$C NMR (75.4 MHz, $CDCl_3$) d 12.0, 18.7, 20.7, 20.9, 27.2, 36.7, 52.9, 59.9, 100.4, 109.0, 123.6, 124.1, 126.7, 126.8, 133.48, 133.51. m/e 284 (M+, 41), 157 (100), 184 (66), 156 (35), 168 (19), 129 (10).

The residual fractions from above chromatography contained cis-(5-methyl-5,6,7,8-tetrahydro-1H-benzo[f]-indol-6-yl)-dipropylamine (11d, Chart 2). MS (EI) m/e 284 (M+, 52), 184 (100), 255 (63), 157 (63), 156 (35), 168 (22), 129 (11).

EXAMPLE 16 cis-7-Dipropylamino-6-methyl-6,7,8,9-tetrahydro-3H-benzo[e]-indole-1-carbaldehyde (10d, Chart 2) ($R_1R_2$ n-propyl; $R_3$ $CH_3$; $R_4$ $CH_2$; YZ (b) ; $R_5$ H; $R_6$ CHO)

This compound was prepared according to the procedure described for 4a, (Chart 1).

$^1$H NMR (300 MHz, $CDCl_3$) d 0.88 (t, 6H), 1.23 (d, 3H), 1.51 (m, 4H), 1.90 (m, 1H), 2.12 (m, 1H), 2.64 (m, 4H), 2.98 (m, 1H), 3.22 (m, 2H), 3.61 (dd, 1H), 7.05 (d, 1H), 7.26 (d, 1H), 7.93 (s, 1H), 10.13 (s, 1H), 10.22 (sb, 1H); $^{13}$C NMR (75.4 MHz, $CDCl_3$) d 12.0, 18.5, 20.3, 20.9, 30.3, 37.2, 52.6, 59.4, 110.1, 121.1, 123.7, 126.4, 129.1, 135.3, 135.6, 137.3, 185.9; MS (EI) m/e 312 (M+, 8), 213 (100), 212 (25), 184 (23), 100 (15), 156 (15), 198 (14), 255 (12).

EXAMPLE 17

Di-n-propyl-(6,7,8,9-tetrahydronaphtho[1,2-b]furan-7-yl)-amine. (15a, Chart 3) ($R_1R_2$ n-propyl; $R_3$ hydrogen; $R_4$ $CH_2$; YZ (c); $R_5R_6$ H)

Step A: 6-Di-n-propylamino-5,6,7,8-tetrahydronaphthylenee-1-ol. (13a, Chart 3)

This compound was prepared according to Hacksell et al. (J. Med. Chem. 22:1469 (1979)).

Step B: [5-(2,2-Diethoxy-ethoxy)-1,2,3,4-tetrahydronaphthylenee-2-yl]-dipropyl-1-amine. (14a, Chart 3)

A solution of 6-di-n-propylamino-5,6,7,8-tetrahydronaphthylenee-1-ol, 13a (Chart 3) (128 mg, 0.52 mmol) in 20 mL acetonitrile was treated with sodium hydride (55% in oil) (50 mg, 1.12 mmol). A solution of bromoacetaldehyde diethylacetal (112 mg, 0.57 mmol) in 5 ml acetonitrile was added and the mixture was refluxed for 3 days. After cooling, the reaction mixture was evaporated to a residue which was dissolved in water/ethyl acetate. After extraction two additional times, the combined organic extracts were dried (magnesium sulfate), filtered and evaporated to yield a residue of the raw material as an oil (210 mg, 110%). This material was used without further purification in the next step.

MS m/e 363 (M+, 15), 145 (100), 334 (87), 103 (74), 73 (65), 126 (58), 171 (55), 218 (45).

Step C: Di-n-propyl-(6,7,8,9-tetrahydronaphtho[1,2-b] furan-7-yl)-amine. (15a, Chart 3)

A solution of [5-(2,2-diethoxy-ethoxy)-1,2,3,4-tetrahydronaphthylenee-2-yl]-dipropyl-1-amine, 14a (Chart 3) (210 mg, 0.57 mmol) in dichloromethane (20 mL) was treated with 1,2 eq acetic acid followed by bromotrifluoride etherate (330 mg, 2.4 mmol). The reaction mixture was stirred at room temperature for two days and the solvent then evaporated. Water was added and the resulting suspension was basified (5M sodium hydroxide). After extraction (three times ethyl acetate) the solution was dried (magnesium sulfate, filtered and evaporated to yield 160 mg (100%) of the crude product, which was purified on silica (dichloromethane/methanol, 19:1) to yield 25 mg (16%) of the pure compound as a colorless oil.

$^1$H NMR (200 MHz, $CDCl_3$) d 0.90 (t, 6H), 1.50 (sixt, 4H), 1.70 (oct, 1H), 2.2 (br.d, 1H), 2.55 (t, 4H), 2.8–3.2 (m's, 4H), 3.3 (d of d, 1H), 6.70 (d, J=2.1 Hz, 1H), 6.98 (d, J=8.1 Hz, 1H), 7.34 (d, J=8.0 Hz, 1H), 7.56 (d, J=2.2 Hz, 1H); $^{13}$C NMR (75.4 MHz, $CDCl_3$) d 11.8 ($CH_3$), 21.7 ($CH_2$), 23.4 ($CH_2$), 25.0 ($CH_2$), 31.5 (CH2), 52.6 ($CH_2$), 57.1 (CH), 106.6 (CH), 118.3 (CH), 120.2 (C), 124.3 (CH), 124.4 (C), 132.5 (C), 144.1 (CH), 153.4 (C); MS m/e 271 (M+, 9), 171 (100), 242 (45), 128 (26), 115 (18), 141 (18), 145 (15).

EXAMPLE 18

S-(−)-7-Dipropylamino-6,7,8,9-tetrahydro-3H-benzo [e]indole-1-carbaldehyde (10a:1, Chart 2)

This compound was synthesized from 9a:1 according to the procedure given for compound 4a (Chart 1)

$^1$H NMR (300 MHz, $CDCl_3$) δ 0.90 (t, 6H), 1.50 (m, 4H), 1.70 (m, 1H), 22.1 (m, 1H), 2.55 (m, 4H), 2.80–3.10 (m, 3H), 3.20 (m, 1H), 3.60 (m, 1H) 7.04 (d, 1H), 7.18 (d, 1H), 7.90 (s, 1H), 9.12 (br s, 1H), 10.15 (s, 1H); $^{13}$C NMR (75.4 MHz, $CDCl_3$) δ 12.0, 22.0, 25.8, 30.2, 33.1, 52.7, 56.6, 109.5, 121.2, 123.8, 126.3, 130.2, 131.1, 134.3, 135.7, 185.5. MS m/z (relative intensity, 70 eV) 298 ($M^+$, 43), 199 (100), 198 (91), 269 (81), 170 (45), 100 (18). $[α]_D^{20}$ −58.5° (c=1.0, MeOH)

EXAMPLE 19

Di-n-propyl-(6,7,8,9-tetrahydronaphtho[2,1-b]furan-7-yl)-amine (15b, Chart 3) and Di-n-propyl-(5,6,7,8-tetrahydronaphtho[2,3-b]furan-6-yl)-amine (15c, Chart 3)

Step A [6-(2,2-Diethoxy-ethoxy)-1,2,3,4-tetrahydronaphthylene-2-yl]-dipropyl-1-amine (14b, Chart 3).

Sodium hydride (244 mg, 55–60% in oil, 5.8 mmol) was washed with hexane two times and then slurried in acetinitrile (20 mL). Dipropyl-(6-hydroxy-1,2,3,4-tetrahydronaphthylene-2-yl)-amine (1.26 mg, 5.1 mmol) was added, followed by 2-bromo-acetaldehyde diethylacetal (1.1 g, 5.6 mmol). The mixture was refluxed for 2 days, evaporated and redissolved in water/ethyl acetate. The organic solution was dried (magnesium sulfate), filtered and evaporated to yield 1.86 g (100%) of the desired compound.
Step B Di-n-propyl-(6,7,8,9-tetrahydronaphtho[2,1-b]furan-7-yl)-amine (15b Chart 3) and Di-n-propyl-(5,6,7,8-tetrahydronaphtho[2,3-b]furan-6-yl)-amine. (15c Chart 3)

To a solution of [6-(2,2-diethoxy-ethoxy)-1,2,3,4-tetrahydronaphthylene-2-yl]-dipropyl-1-amine (14b Chart 3) (1.86 g, 5.1 mmol) and acetic acid (250 µL) in dichloromethane (100 mL) was added borontrifluoride etherate (2.91 g, 2.51 mL, 20.4 mmol). The resulting mixture was stirred over night and evaporated. Sodium hydroxide (5M) and ethyl acetate was added and the mixture was shaken. The aqueous phase was extracted two additional times using ethyl acetate. The combined organic extracts were dried (magnesium sulfate), filtered and evaporated to a residue of 1.4 g, which was further purified on silica yielding 220 mg(16%) of the two isomers.: MS m/z (relative intensity, 70 eV) 271 ($M^+$, 28), 171 (100), 242 (79), 128 (19).

EXAMPLE 20 cis-(6S-Methyl-6,7,8,9-tetrahydro-naphto[1,2-b]furan-7R-yl]-dipropyl-amine (15d, Chart 3)

Step A cis-[5-(2,2-Diethoxy-ethoxy)-1S-methyl-1,2,3,4-tetrahydro-naphthylene-2R-yl]-dipropyl-amine (14c, Chart 3)

This compound was prepared as described for 14a from cis-(+)-(5-hydroxy-1S-methyl-1,2,3,4-tetrahydro-naphthylene-2R-yl)-dipropyl-amine (450 mg, 1.72 mmol, for preparation see Johansson et. al. *J. Med. Chem.* 1987, 30, 602–611). The residue was used without further purification (700 mg); MS m/z (relative intensity, 70 eV)) 377 ($M^+$ 34), 348.5 (100), 232 (80), 185 (23), 159 (51).
Step B cis-(6S-Methyl-6,7,8,9-tetrahydro-naphto[1,2-b]furan-7R-yl)-dipropyl-amine (15d, Chart 3).

This compound was prepared as described for 15a from cis-[5-(2,2-diethoxy-ethoxy)-1S-methyl-1,2,3,4-tetrahydro-naphthylene-2R-yl]-dipropyl-amine (648 mg, 1.72 mmol). Purification of the crude reaction mixture by flash chromatography ($CH_2Cl_2$/MeOH, 9/1 (v/v))afforded 65.8 mg (13.4%) of pure 16d as an oil;
$^1$H NMR (300 MHz, $CDCl_3$) δ 0.9 (t, 6H), 1.2 (d, 3H), 1.5 (m, 4H), 1.9 (m, 1H), 2.55–2.75 (m, 4H), 2.8–3.1 (m, 3H), 3.25 (m, 2H), 6.72 (d, J=2.2 Hz, 1H), 7.0 (d, J=8 Hz, 1H), 7.4 (d, J=8 Hz, 1H), 7.6 (d, J=2 Hz, 1H); MS m/z (relative intensity, 70 eV) 285 ($M^+$ 36), 256 (100), 185 (96), 158 (36), 128 (16).

EXAMPLE 21

(7,8-Dihydro-6H-1-oxa-as-indacen-7-yl)-dipropyl-amine (15e, Chart 3)

Step A [4-(2,2-Diethoxy-ethoxy)-indan-2-yl]-dipropyl-amine (14d, Chart 3)

This compound was prepared as described for 14a from (4-hydroxy-indan-2-yl)-dipropyl-amine (220 mg, 1.05 mmol). The residue was used without any further purification (340 mg); MS m/z (relative intensity, 70 eV) 349.5 ($M^+$ 6), 321 (22), 320 (100), 103 (10.5), 72 (10).
Step B (7,8-Dihydro-6H-1-oxa-as-indacen-7-yl)-dipropyl-amine (15e, Chart 3))

This compound was prepared as described for 15a from [4-(2,2-Diethoxy-ethoxy)-indan-2-yl]-dipropyl-amine (340 mg). MS m/z (relative intensity, 70 eV) 257 ($M^+$ 14), 228 (100), 204 (21), 157 (49), 128 (19.6)

EXAMPLE 22

(7,8-Dihydro-6H-3-oxa-as-indacen-7-yl)-dipropyl-amine (15f, Chart 3) and (6,7-Dihydro-5H-1-oxa-s-indacen-6-yl)-dipropyl-amine (15 g, Chart 3)

Step A [5-(2,2-Diethoxy-ethoxy)-indan-2-yl]-dipropyl-amine (14e, Chart 3)

This compound was prepared as described for 14a from (5-hydroxy-indan-2-yl)-dipropyl-amine (220 mg, 1.05 mmol). The residue was used without any further purification (330 mg); MS m/z (relative intensity, 70 eV) 349.5 ($M^+$ 6.8), 321 (22), 320 (100), 133 (28), 103 (10.8), 61 (8.8).
Step B (7,8-Dihydro-6H-3-oxa-as-indacen-7-yl)-dipropyl-amine (15 f, Chart 3) and (6,7-Dihydro-5H-1-oxa-s-indacen-6-yl)dipropyl-amine (15 g, Chart 3)

This compound was prepared as described for 15a from [5-(2,2-Diethoxy-ethoxy)-indan-2-yl]-dipropyl-amine (340 mg). A mixture of the two regio-isomers were obtained in a 1:3 relationship according to gC/MS. Purification of the crude reaction mixture by flash chromatography (dichloromethane/methanol, 9/1 (v/v)) afforded 11 mg (13.4%) of the pure mixture as an oil; MS m/z (relative intensity, 70 eV) 257 ($M^+$ 9.2), 228 (100), 157 (53), 129 (19), 128 (18.6)

EXAMPLE 23

7-Di-propylamino-1,6,7,8-tetrahydro-9-oxa-1-azacyclopenta[α]naphthylenee-3-carbaldehyde (4b, Chart 1)

To dry N,N-dimethyl formamide (6.5 mL) at 0° C. was added phosphorous oxychloride (0.24 mL, 2.64 mmol). The solution was stirred in an ice bath for 10 min. Thereafter di-propyl-(1,6,7,8-tetrahydro-9-oxa-1-azacyclopenta[α] naphthylene-7-yl)amine (144 mg, 52.9 mmol) dissolved in dry dimethylfomamide (6.5 mL) was added. The solution was stirred for 10 min at 0° C. and for additional 30 min at room temperature. The reaction mixture was placed in an oil bath and stirred at 50° C. for 2h under nitrogen. The solution was allowed to reach room temperature. Aqueous sodium hydroxide was added (30 ml, 5%) and the mixture was stirred for 30 min at 50° C. Additional water (25 mL) was added and the mixture extracted with dichloromethane. The phases were separated and the organic layer was dried (sodium sulfate) and evaporated. The crude product was purified using Silica column chromatography with dichloromethane/methanol (30:1) as eluant, yielding 60 mg (38%) of pure 7-di-propylamino-1,6,7,8-tetrahydro-9-oxa-1-azacyclopenta[α]naphthylenee-3-carbaldehyde.:
$^1$H NMR (300 MHz, $CDCl_3$) δ 0.91 (t, 6H), 1.46 (m, 4H), 2.53 (m, 4H), 2.96 (d, 2H), 3.27 (m, 1H), 3.93 (t, 1H), 4.42 (d of d, 1H), 6.96 (d, J=8 Hz, 1H), 7.69–7.80 (m, 2H), 9.1 (s, 1H), 10.0 (s, 1H); $^{13}$C NMR (75.4 MHz, $CDCl_3$) δ 11.7, 21.8, 27.5, 52.8, 53.6, 68.5, 113.7, 116.0, 120.1, 124.2, 125.1, 126.5, 134.4, 140.3, 185.3; MS m/z (relative intensity, 70 eV) 300 (M+, 71), 98 (100), 70 (74), 200 (64), 127 (55).

EXAMPLE 24

(±)-Propyl-(6,7,8,9)-tetrahydro-3H-benzo[3]indol-7-yl)-amine (9e:1, Chart 2)

This compound was prepared from a diastereomeric mixture of 2-[6-(1-Phenyl-ethylamino)-5,6,7,8-tetrahydro-naphthylenee-2-yl]isoindole-1,3-diones (8.69 g, 21.9 mmol), using the same reaction sequence as previously described for the optically active counterparts. The yeild of the title compound, after chromatography on a silica column, was 1.11 g.:
$^1$H NMR (300 MHz, $CDCl_3$) δ 0.95 (t, 3H), 1.57 (q, 2H), 1.72 (m, 1H), 2.20 (m, 1H), 2.73 (m, 3H), 2.90–3.22 (m, 4H), 6.50 (m, 1H), 6.94 (d, 1H), 7.17 (m, 2H), 8.48 (sb, 1H); $^{13}$C NMR (75.4 MHz, $CDCl_3$) δ 11.9, 23.5, 25.4, 29.5, 36.6, 49.0, 54.0, 100.3, 108.9, 123.6, 123.9, 125.6, 126.9, 127.6, 133.8; MS (EI) m/z (relative intensity, 70 eV) 228 (M+, 30), 143 (100), 168 (46), 169 (42), 170 (34), 144 (22), 154 (19), 115 (15), 167 (15), 199 (12), 155 (10), 197 (7).

EXAMPLE 25

Methyl-propyl-(6,7,8,9-tetrahydro-3H-benzo[e]indol-7-yl)amine (9f, Chart 2)

To a solution of propyl-(6,7,8,9-tetrahydro-3H-benzo[3]indol-7-yl)amine (125 mg, 0.54 mmol) and formaldehyde (0.5 mL 37% in water) in tetrahydrofuran (10 mL) was added sodium triacetoxy borohydride (220 mg, 1.03 mmol). After stirring in room temperature for 0.5 hr., water and diethyl ether was added followed by 3M sodium hydroxide to basify the aqueous phase. After shaking and separation the aqueous phase was extracted two additional times with diethyl ether. The combined organic solution was dried (magnesium sulfate) filtered and evaporated to yield 108 mg (83%) of the pure product as an oil:

$^1$H NMR (300 MHz, CDCl$_3$) δ 0.95 (t, 3H), 1.62.sxt (2), 1.75 (oct, 1H), 2.2 (br d, 1H), 2.42 (s, 3H), 2.60 (t, 2H), 2.8–3.1 (m, 4H), 3.2 (d of d, 1H), 6.50 (s 1H), 6.92 (d, J=8.3 Hz, 1H), 7.16 (m, 1H), 7–18 (d, J=8.3 Hz, 1H), 8.90 (br s, 1H); $^{13}$C NMR (75.4 MHz, CDCl$_3$) δ 11.9, 20.5, 25.5, 26.8, 30.8, 37.5, 55.6, 59.7, 100.1, 109.0, 123.6, 123.8, 125.9, 126.8, 127.4, 133.8; MS m/z (relative intensity, 70 eV) 242 (M$^+$, 65), 170 (100), 143 (97), 213 (50), 168 (32), 115 (17).

EXAMPLE 26

Methyl-(1-methylsulfanyl-6,7,8,9-tetrahydro-3H-benzo[e]indol-7-yl)propylamine (10e, Chart 2)

Sulfuryl chloride (14.0 μL, 14.5 mg, 0.15 mmol) was added to a solution of dimethyl disulfide (12.4 μL, 20.8 mg, 0.15 mmol) in dichloromethane (3 mL) at 0° C. After stirring for 15 minutes, this solution was added to an ice-cooled solution of methyl-propyl-(6,7,8,9-tetrahydro-3H-benzo[3]indol-7-yl)amine in dichloromethane (10 mL). The resulting solution was stirred at room temperature for 2 hours. Water, followed by 3M sodium hydroxide was added and the mixture was shaken. The orgnic phase was dried (magnesium sulfate), filtered and evaporated to yield a residue of 55 mg (86%).:

MS m/z (relative intensity, 70 eV) 288 (M$^+$, 100), 216 (94), 259 (58), 207 (58) 174 (37).

EXAMPLE 27

Propyl-(6,7,8,9-tetrahydro-3H-benzo[e]indol-7-yl)-(2-thiophen-2-yl-ethyl)-amine (9 g, Chart 2)

Step A N-Propyl-N-(6,7,8,9-tetrahydro-3H-benzo[e]indol-7-yl)-2-thiophen-2-yl-acetamide.

A mixture of propyl-(6,7,8,9-tetrahydro-3H-benzo[e]indol-7-yl)amine (99 mg, 0.43 mmol), triethyl amine (200 μL) and thiophene-2-acetylchloride (94 μL, 121 mg, 0.75 mmol) in dichloromethane (15 mL) was stirred for two days. Water was added and the mixture shaken. The organic phase was washed (10% sodium carbonate), dried (magnesium sulfate), filtered and evaportated.:

Ms m/z (relative intensity, 70 eV) 169 (M$^+$-N-propyl-2-tiophenacetamide, 100), 143 (8), 154 (7), 97 (6), 207 (1)

Step B Propyl-(6,7,8,9-tetrahydro-3H-benzo[e]indol-7-yl)-(2-thiophen-2-yl-ethyl)-amine (9 g, Chart 2).

This material was slurried in diethyl ether (50 mL). Lithium aluminum hydride (110 mg, 2.9 mmol) was added inportions. The mixture was then stirred for 3 hours. The product was completely soluble in diethyl ether in contract to the amide. Water (110 μL) followed by 15% sodium hydroxide (110 μL) and water (330 μL) was added. After stirring for 30 minutes, the solid material was filtered off and the resulting ethereal solution was evaporated to yield 135 mg (99%) of the products as an oil.:

MS m/z (relative intensity, 70 eV) 241 (M$^+$-thiophenemethylene, 68), 170 (100), 154 (11).

EXAMPLE 28

7-[Propyl-(2-thiophene-2-yl-ethyl)-amino]-6,7,8,9-tetrahydro-3H-benzo[e]indole-1-carbaldehyde (10f, Chart 2)

A cooled (−5° C.) solution of propyl-(6,7,8,9-tetrahydro-3H-benzo[e]indol-7-yl)-(2-thiophen-2-yl-ethyl)amine (9 g, Chart 2) (94 mg, 0.28 mmol) in N, N-dimethylformamide (3 mL) was added to a cooled (−5° C.) solution of phosphorous oxychloride in N,N-dimethylformamide (3 mL). The mixture was stirred at ambient temperature for 0.5 hour, then heated at 50° C. for 2 hours. After cooling, 15% sodium hydroxide was added and the mixture was heated at 50° C. for 15 minutes and then cooled. The aqueous mixture was extracted with ethyl acetate and the organic solution was dried (magnesium sulfate), filtered and evaporated to a residue of 84 mg (82%) of the desired material.

MS m/z (relative intensity, 70 eV) 269 (M$^+$-thiophenemethylene, 100), 198 (77), 170 (23), 270 (20), 155 (11)

EXAMPLE 29

Cyclobutylmethyl-propyl-(6,7,8,9-tetrahydro-3H-benzo[e]indol-7-yl)lamine (9h, Chart 2)

Step A Cyclobutanecarboxylic acid propyl-6,7,8,9-tetrahydro-3H-benzo[e]indol-7-yl)-amide.

A solution of propyl-(6,7,8,9-tetrahydro-3H-benzo[e]indol-7-yl)amine (100 mg, 0.44 mmol), triethyl aminee and cyclobutanecarbonyl chloride (60 mg, 50 mmol) in dichloromethane was stirred for 1 hour at room temperature. Water was added and the mixture shaken. The organic phase was washed (10% sodium carbonate), dried (magnesium sulfate), filtered and evaporated to yield 134 mg (100%) of the title compound:

MS m/z (relative intensity, 70 eV) 310 (M$^+$, <1), 169 (100), 55 (10), 143 (8).

Step B Cyclobutylmethyl-propyl-(6,7,8,9-tetrahydro-3H-benzo[e]indol-7-yl)amine (9h, Chart 2).

Cyclobutanecarboxylic acid propyl-6,7,8,9-tetrahydro-3H-benzo[e]indol-7-yl)-amide (134 mg, 0.44 mmol) was dissolved in diethyl ether (20 mL). To this solution lithium aluminum hydride (100 mg, 2.6 mmol) was added in portions. The mixture was stirred for 2 hours. The product was completely soluble in diethyl ether in contrast to the amide. Water (100 μL) followed by 15% sodium hydroxide (100 μL) and water (300 μL) was added. After stirring for 15 minutes, the solid material was filtered off and the resulting ethereal solution was evaporated to yield 108 mg (83%) of the product as an oil.:

MS m/z (relative intensity, 70 eV) 296 (M$^+$, 43), 170 (100), 241 (50), 267 (36), 143 (28).

EXAMPLE 30

(1-Chloro-6,7,8,9-tetrahydro-3H-benzo[e]indol-7-yl) cyclobutylmethyl-propylamine. (10g, Chart2)

A solution of cyclobutylmethyl-propyl-(6,7,8,9-tetrahydro-3H-benzo[e]indol-7-yl)amine 48 mg, 0.16 mmol) and N-chlorosuccinimide (35 mg, 0.26 mmol) in tetrahydrofuran (5 mL) was stirred at room temperature for 1 day. After pouring the reaction mixture into water, extraction (diethyl ether), drying (magnesium sulfate), filtering, and evaporation yielded 43 mg (80%) of the desired compound.:

MS m/z (relative intensity, 70 eV) 330 (M⁺, 36), 330 (M⁺+2, 12), 204 (100), 275 (65), 169 (40), 301 (39).

EXAMPLE 31

Dipropylamino-1,3,6,7,8,9-hexahydro-benzo[e]
indol-2-one (10h, Chart 2).

To a solution of dipropyl-(6,7,8,9-tetrahydro-3H-benzo[e]indol-7-yl)amine (200 mg, 0.74 mmol), water (5 ML) in acetic acid (50 mL) was added dropwise to a solution of pyridiniumhydrobromide perbromide (310 mg, 0.91 mmol) in acetic acid (100 mL). The solution was heated and stirred at 80° C. over night. After cooling the solution was evaporated to an aqueous residue, which was basified (10% sodium carbonate) and extracted three times with ethyl acetate. The organic extract was dried (magnesium sulfate), filtered and evaporated to yield 210 mg (100%) of the material.:

MS m/z (relative intensity, 70 eV) 286 (M⁺, 25), 186 (100), 257 (81), 207 (11).

EXAMPLE 32

1-(7-Dipropylamino-6,7,8,9-tetrahydro-3H-benzo[e]
indol-1-yl)-2,2,2-trifluoro-ethanone (10i, Chart 2).

To an ice-cooled solution of dipropyl-(6,7,8,9-tetrahydro-3H-benzo[e]indol-7-yl)amine (150 mg, 0.56 mmol) in dimethyl formamide (5 mL) in an inert atmosphere was added trifluoroacetic anhydride (300 μL, 447 mg mg, 2.12 mmol) and the following mixture was stirred over night at room temperature. Water was added and the aqueous solution was washed with diethyl ether. After basification (5% sodium hydroxide), the aqueous solution was extracted two times with diethyl ether and one time with ethyl acetate. The combined organic extract was dried (magnesium sulfate), filtered and evaporated to yield a residue which was purified in silica using methanol as eluant. The pure fractions were collected and evaporated to yield 130 mg (63%) of the pure material.:

¹H NMR (300 MHz, CDCl₃) δ 0.90 (t, 6H), 1.50 (sxt, 4H), 1.6 (m, 1H), 2.15 (br d, 1H), 2.55 (t, 4H), 2.8–3.1 (m, 3H), 3.3 (m, 1H), 3.55 (br d, 1H), 7.09 (d, J=8.4 Hz, 1H), 7.20 (d, J=8.4 Hz, 1H), 8.05 (d, J=1.8 Hz, 1H), 9.5 (br s, 1H); ¹³C NMR (75.4 MHz, CDCl₃) δ 12.0, 21.8, 257.7, 29.8, 33.5, 52.6, 56.4, 109.4, 112.1, 117.5 (q), 124.4, 127.5, 131.6, 132.1, 135.2, 135.5, 174.8 (q); MS m/z (relative intensity, 70 eV) 366 (M⁺, 33), 337 (100), 266 (92), 169 (38).

EXAMPLE 33

1-(7-Dipropylamino-6,7,8,9-tetrahydro-3H-benzo[e]
indol-1-yl)propan-1-one (10j, Chart 2)

A mixture of dipropyl-(6,7,8,9-tetrahydro-3H-benzo[e]indol-7-yl)amine (70 mg, 0.26 mmol) and phosphorous oxychloride (48 μL, 80 mg, 0.52 mmol) in N,N-dimethyl propionamide (250 μL) was heated at 80° C. for 6 hours. After cooling 5M sodium hydroxide was added and the mixture was heated again for 0.5 hour. After cooling, the mixture was extracted 3 times with ethyl acetate, dried (magnesium sulfate), filtered and evaporated to yield a residue to which 99% ethanol was added. This was then evaporated to dryness. A few repetions of the last procedure yielded a residue of 86 mg (100%) of the product.:

MS m/z (relative intensity, 70 eV) 326 (M⁺, 57), 297 (100), 226 (92), 170 (42), 196 (22).

EXAMPLE 34

1-(7-Dipropylamino-6,7,8,9-tetrahydro-3H-benzo[e]
indol-1-yl)ethanone (10k, Chart 2).

A mixture of dipropyl-(6,7,8,9-tetrahydro-3H-benzo[e]indol-7-yl)amine (55 mg, 0.20 mmol) and phosphorous oxychloride (130 μL, 213 mg, 1.39 mmol) in N,N-dimethylacetamide (200 μL) was heated at 80° C. for 4 hours. After cooling 5M sodium hydroxide was added and the mixture was heated again for 0.5 hours. After cooling the mixture was extracted 3 times with ethyl acetate, dried (magnesium sulfate), filtered and evaporated to yield a residue to which 99% ethanol was added. This was then evaporated to dryness. A few repetitions of the last procedure yielded a residue of 56 mg (89%) of the product, which was further purified on silica using methanol as eluant to give the pure material as a solid.:

m.p. 196°–197° (free base); ¹H NMR (300 MHz, CDCl₃) δ 0.90 (t, 6H), 1.50 (sxt, 4H), 1.55 (m, 1H), 2.15 (br d, 1H), 2.5 (t, 4H), 2.55 (s, 3H), 2.8–3.1 (m, 3H), 3.3 (m, 1H), 3.55 (br d, 1H), 7.02 (d, J=8.3 Hz, 1H), 7.14 (d, J=8.3 Hz, 1H), 7.77 (d, J=2.7 Hz, 1H), 8.9 (br s, 1H); ¹³C NMR (75.4 MHz, CDCl₃) δ 12.0 (CH₃), 22.0 (CH₂), 25.9 (CH₂), 28.9 (CH₃), 30.0 (CH₂), 33.5 (CH₂), 52.7 (CH₂), 56.7 (CH), 109.0 (CH), 120.5 (C), 123.7 (C), 126.5 (CH), 130.7 (C), 131.4 (C), 132.4 (CH), 135.5 (C), 193.1 (C); MS m/z (relative intensity, 70 eV) 312 (M⁺, 62), 283 (100), 212 (93), 170 (48).

EXAMPLE 35

6-Dipropylamino-1,3,5,6,7,8-hexahydro-benzo[f]
indol-2-one (12b, Chart 2)

To a solution of di-n-Propyl-(5,6,7,8-tetrahydro-1H-benzo[f]indol-6-yl)amine (30 mg, 0.11 mmol) and water (1 mL) in acetic acid (10 mL) was added pyridiniumperbromide hydrobromide (40 mg, 0.12 mmol) in acetic acid at room temperature. The resulting mixture was heated at 80° C. over night. After cooling, the solution was evaporated to yield an aqueous residue, which was basified using 3M sodium hydroxide. Extraction (ethyl acetate), drying (magnesium sulfate, filtering and evaporation yeilded 26 mg (83%) the desired compound:

MS m/z (relative intensity, 70 eV) 286 (M⁺, 32), 186 (100), 257 (74), 158 (12).

EXAMPLE 36

1-(6-Dipropylamino-5,6,7,8-tetrahydro-1H-benzo[f]
indol-3-yl)propan-1-one (12c, Chart 2)

A mixture of dipropyl-(6,7,8,9-tetrahydro-3H-benzo[e]indol-7-yl)amine (60 mg, 0.22mmol) and phosphorous oxychloride (41 μL, 68 mg, 0.44 mmol) in dimethylpropionamide (200 μL) was heated at 80° C. for 2 hours. After cooling 5M sodium hydroxide (7 mL) was added and the mixture was heated again at 80° C. for 15 minutes. After cooling the mixture was extracted 3 times with ethyl acetate, dried (magnesium sulfate), filtered and evaporated to yield a residue to which 99% ethanol was added. This was then evaporated to dryness. A few repetitions of the last procedure yielded a residue of 55 mg (77%) of the product.:

MS m/z (relative intensity, 70 eV) 326 (M⁺, 43), 226 (100), 297 (92), 170 (25).

EXAMPLE 37

9-Bromo-6-dipropylamino-5,6,7,8,-tetrahydro-1H-
benzo[f]indole-1,2-dione (8e, Chart 2) and 4-
Bromo-7-dipropylamino-6,7,8,9-tetrahydro-3H-
benzo[e]indole-1,2-dione (7e, Chart 2)

Step A N-(6-Dipropylamino-5,6,7,8-tetrahydro-naphthylene-2-yl)-acetamide.

To a cold stirred solution (≈0° C.) of N,N-dipropyl-1,2,3,4-tetrahydro-naphthylenee-2,6-diamine (226 mg, 0.92 mmol) in dichloro methane (5 mL) was added acetyl chloride (100 µL), 1.37 mmol) followed by triethyl amine (220 µL), 1.57 mmol). The mixture was then allowed to reach ambient temperature and was stirred for an additional 30 minutes. The solvent was removed in vacuo and the residue taken up in dilute hydrochloric acid (10 mL). The aqueous solution was washed with ethyl acetate (2×10 mL) and then basified with a 15% sodium hydroxide solution. Extraction with ethyl acetate, drying over magnesium sulfateand removal of the solvent yielded a pale yellow solid (220 mg, 83%). This material was used in the subsequent step without further purification.:

MS (EI) m/z (relative intensity, 70 eV) 288 (M$^+$, 37), 259 (100), 188 (72), 146 (44), 144 (16), 126 (14).

Step B 5-Bromo-N,N-dipropyl-1,2,3,4-tetrahydro-naphthylenee-2,6-diamine (6e, Chart 2) and 7-Bromo-N,N-dipropyl-1,2,3,4-tetrahydro-naphthylenee-2,6-diamine (6f, Chart 2).

A stirred solution of N-(6-Dipropylamino-5,6,7,8-tetrahydro-naphthylene-2-yl)-acetamide (450 mg, 1.56 mmol) in acetic acid (10 mL) was heated to 90° C. Then neat bromine (1.1 g, 6.88 mmol) was added in one portion. Stirring was maintained for 2 minutes after this addition and then the mixture was cooled. Saturated aqueous sodium bisulfite was added (10 ml) followed by the addition of 5M sodium hydroxide (50 mL). The aqueous solution was extracted with ethyl acetate (2×20 mL), dried over magnesium sulfate and evaporated to yield a 4:1 mixture of the intermediate N-(3-Bromo-6-dipropylamino-5,6,7,8-tetrahydro-naphthylenee-2-yl)-acetamide and N-(1-Bromo-6-dipropylamino-5,6,7,8-tetrahydro-naphthylenee-2-yl)-acetamide as an oil (500 mg). The mixture of bromo acetamides was taken up in 6M hydrochloric acid and heated at reflux temperature for 1 hour. After cooling, the acidic solution was basified by addition of 5M sodium hydroxide. The solution was then extracted with ethyl acetate (3×20 mL), the combined extracts washed with brine, drying over magnesium sulfate, and the solvent removed in vacco. The resulting dark oil consisted of an isomeric mixture of the 7- and 5-bromo anilines in a 4:1 ratio (370 mg, 73%). All attempts to separate these isomers failed and the mixture was used in the subsequent step without further purification.:

(6e, Chart 2) $^1$H NMR (300 MHz, CDCl$_3$) δ 0.88 (t, 6H), 1.45 (m, 4H), 2.05 (m, 1H), 2.45 (m, 4H), 2.6–2.8 (m, 3H), 2.88 (m, 1H), 3.02 (m, 1H), 4.00 (sb, 2H), 1H), 6.59 (d, 6.85 (d, 1H); MS (EI m/z (relative intensity, 70 eV) 324 (M$^+$, 42), 326 (M$^+$+2, 41), 224 (100), 226 (96), 295 (88), 297 (86), 145 (58), 144 (38), 130 (20), 199 (12).

(6f, Chart 2). $^1$H NMR (300 MHz, CDCl$_3$) δ 0.88 (t, 6H), 1.45 (m, 4H), 2.05 (m, 1H), 2.45 (m, 4H), 2.6–2.8 (m, 3H), 2.88 (m, 1H), 3.02 (m, 1H), 3.87 (sb, 2H), 6.49 (s, 1H), 7.13 (s, 1H); MS (EI) m/z (relative intensity, 70 eV) 324 (M$^+$, 42), 326 (M$^+$+2, 41), 224 (100), 226 (96), 295 (88), 297 (86), 145 (58), 144 (38), 130 (20), 199 (12).

Step C 9-Bromo-6-dipropylamino-5,6,7,8,-tetrahydro-1H-benzo[f]indole-1,2-dione (ie, Chart 2) and 4-Bromo-7-dipropylamino-6,7,8,9-tetrahydro-3H-benzo[e]indole-1,2-dione (7e, Chart 2).:

A 4:1 mixture of 7-Bromo-N,N-dipropyl-1,2,3,4-tetrahydro-naphthylenee-2,6-diamine and 5-Bromo-N,N-dipropyl-1,2,3,4-tetrahydro-naphthylenee-2,6-diamine (4.0 g, 12.3 mmol) was converted into its hydrochloride salt by treatment with ethanolic hydrochloric acid followed by evaporation of the solvent. The resulting salt was dissolved in water (51 mL). To this solution was added chloral hydrate (2.23 g, 13.5 mmol), hydroxyl ammonium chloride (2.71 g, 39 mmol) and anhydrous sodium sulfate (13.7 g). The mixture was then heated at reflux temperature for 1 hour. After cooling ammonium hydroxide (72 mL, 3.2%) was added and the aqueous layer extracted with several portions of ethyl acetate. Drying over magnesium sulfate and removal of the solvent in vacuo yielded 4.0 g of a mixture of N-(1-Bromo-6-dipropylamino-5,6,7,8-tetrahydro-naphthylenee-2-yl)-2-hydroxyimino-acetamide and N-(3-Bromo-6-dipropylamino-5,6,7,8-tetrahydro-naphthylene-2-yl)-2-hydroxyimino-acetamide as a dark oil. This oil was dissolved in an ice cold mixture of sulfuric acid (61 mL) and water (6 mL). The mixture was stirred at ambient temperature for 30 minutes and then heated to 80° C. for another 30 minutes. After cooling, the reaction mixture was poured into a crushed ice water mixture (750 mL) and treated with concentrated ammonium hydroxide until pH=9. The aqueous layer was extracted with several portions of ethyl acetate and dried. Evaporation of the solvent yielded 3.5 g (75%) of a mixture of 9-Bromo-6-dipropylamino-5,6,7,8,-tetrahydro-1H-benzo[f]indole-1,2-dione and 4-Bromo-7-dipropylamino-6,7,8,9-tetrahydro-3H-benzo[e]indole-1,2-dione as a red oil.

EXAMPLE 38

(9-Bromo-5,6,7,8-tetrahydro-1H-benzo[f]indol-6-yl)-dipropyl amine (11b, Chart 2) and 4-Bromo-6,7,8,9-tetrahydro-3H-benzo[e]indol-7-yl-dipropyl-amine (9i, Chart 2).

A diethyl ether solution (50 mL) of a mixture of 9-Bromo-6-dipropylamino-5,6,7,8,-tetrahydro-1H-benzo[f]indole-1,2-dione and 4-Bromo-7-dipropylamino-6,7,8,9-tetrahydro-3H-benzo[e]indole-1,2-dione (3.5 g, 9.3 mmol) was added dropwise to a stirred suspension of lithium aluminum hydride (3.0) g in dry diethyl ether (100 mL). After the addition was completed, stirring was continued for 2 hours at ambient temperature. The reaction was then quenched by the consecutive addition of water (3.0 mL), 15% sodium hydroxide (3.0 mL) and water (9.0 mL). The solid was filtered of through a celite pad and the solvent removed by evaporation in vacuo to yield a blue oil. The off was subjected to chromatography on a silica column to yield 400 mg of pure (9-Bromo-5,6,7,8-tetrahydro-1H-benzo[f]indol-6-yl)-dipropyl amine. The residual fractions were concentrated and chromatographed on a preparative HPLC system to yield a small amount of pure (4-Bromo-6,7,8,9-tetrahydro-3H-benzo[e]indol-70yl)-dipropyl-amine.:

(11b, Chart 2) $^1$H NMR (300 MHz, CDCl$_3$) δ 0.90 (t, 6H), 1.45 (m, 4H), 1.65 (m, 1H), 2.10 (m, 1H), 2.47 (m, 4H), 2.7–3.0 (m, 4H), 3.17 (m, 1H), 6.5 (dd, 1H), 7.16 (dd, 1H), 7.33 (s, 1H), 8.18 (sb, 1H); $^{13}$C NMR (75.4 1MHz, CDCl$_3$) δ 11.9, 22.1, 26.4, 30.3, 32.9, 52.7, 56.8, 102.9, 106.4, 119.7, 124.4, 126.8,129.3, 130.4, 134.0; MS (EI) m/z (relative intensity, 70 eV) 348 (M$^+$,), 350 (M$^+$+2,), 321 (100), 319 (100), 248 (77), 250 (71), 169 (69), 168 (56), 167 (37), 154 (23).

(9i, Chart 2). $^1$H NMR (300 MHz, CDCl$_3$) δ 0.90 (t, 6H), 1.50 (m, 4H), 1.65 (m, 1H), 2.12 (m, 1H), 2.50 (m, 4H), 2.8–3.2 (m, 5H), 6.56 (m, 1H), 7.10 (s, 1H), 7.22 (m, 1H, 8.26 (sb, 1H); MS (EI m/z (relative intensity, 70 eV) 348 (M$^+$, 51), 350 (M$^+$+2, 49), 321 (100), 319 (98), 248 (76), 250 (72), 169 (48), 168 (45), 167 (32), 154 (18), 223 (17).

EXAMPLE 39

9-Bromo-6-dipropylamino-5,6,7,8-tetrahydro-1H-benzo[f]indol-3-carbaldehyde (12d, Chart 2)

A solution of (9-Bromo-5,6,7,8-tetrahydro-1H-benzo[f]indol-6-yl)-dipropyl amine (50 mg, 0.14 mmol) in N,N-dimethyl formamide (3 mL) was cooled to 0° C. To this solution was added a cooled solution of phosphorus oxychloride (26 µL, 0.28 mmol) in N,N-dimethyl formamide (1 mL), which had been prepared 20 minutes previous to use.

The mixture was stirred at ambient temperature for 30 minutes and then for 30 minutes at 50° C. an additional 30 minutes. The reaction mixture was then treated with a 1M sodium hydroxide solution (5 mL) with heating and stirring maintained for an additional hour. After cooling, the solution was diluted with water (25 mL) and extracted with several portions of diethyl ether. The combined etheral extracts were washed with water, brine, dried over magnesium sulfate, and the solvent evaporated. The residue was chromatographed on a silica column, using methanol as the eluant. This was then repeated with diethyl ether as eluant. The yield of the pure title compound was 50 mg (95%).:

$^1$H NMR (300 1MHz, CDCl$_3$) δ 0.87 (t, 6H), 1.46 (m, 4H), 1.68 (m, 1H), 2.10 (m, 1H), 2.48 (m, 4H), 2.7-3.2 (m, 5H), 7.80 (s, 1H), 7.97 (s, 1H), 9.09 (sb, 1H) $^{13}$C NMR (75.4 1MH$_z$, CDCl$_3$) δ 11.9, 21.8, 26.4, 30.2, 32.8, 52.6, 56.5, 106.6, 120.0, 121.1, 123.2, 132.1, 134.0, 134.7, 135.5, 185.3; MS(EI) m/z (relative intensity, 70 eV) 376 (M$^+$, 22), 378 (M$^+$+2, 22), 347 (100, 349 (94), 276 (70), 278 (65), 197 (44), 168 (30), 250 (13).

EXAMPLE 40

6-Dipropyl-amino-1,5,6,7-tetrahydro-1-aza-s-indacene-2,3-dione (8f, Chart 2) and 7-dipropyl-amino-3,6,7,8-tetrahydro-1-aza-as-indacene-1,2-dione (7f, Chart 2)

Step A: Indan-2-yl-propyl-amine (31, Chart D).

A tetrahydrofuran (150 mL) solution of 2-indanone (11.0 g, 92 mmol), propyl amine (12 mL, 146 mmol), sodium triacetoxy borohydride (35.0 g, 165 mmol), and acetic acid (5 mL) was stirred at ambient temperature for 1 hour. The solution was then heated at reflux temperature for 2 hours. After cooling, the solvent was evaporated and the residue taken up in concentrated hydrochloric acid (40 mL). The acidic solution was washed with diethyl ether and then basified (10M sodium hydroxide). Extraction of the aqueous layer with ether, drying over anhydrous sodium carbonate and removal of the solvent yielded 10.9 g of the title compound as a yellow oil (75%).:

$^1$H NMR (300 MHz, CDCl$_3$) δ 0.92 (t, 3H), 1.55 (m, 2H), 2.65 (t, 2H), 2.76 (dd, 2H), 3.18 (dd, 2H), 3.62 (m, 1H), 7.14 (m, 4H); $^{13}$C NMR (75.4 MHz, CDCl$_3$) δ 11.9, 23.4 40.0, 50.2, 59.6, 124.6, 126.3, 141.8; MS (EI) m/z (relative intensity, 70 eV) 175 (M$^+$, 212), 117 (100), 146 (92), 115 (49), 116 (21), 91 (19), 130 (17), 131 (15), 7712.

Step B: N-Indan-2-yl-N-propyl-propionamide (32, Chart 2).

Propionic acid chloride (2 mL, 2.1 g, 23 mmol) was added dropwise to a solution of indan-2-yl-propylamine (4.0 g, 23 mmol) and triethyl amine in dichloromethane (50 mL). The reaction mixture was stirred at room temperature for 2 hours. Aqueous (10%) sodium carbonate was added and the mixture was shaken. The organic phase was dried (magnesium sulfate), filtered and evaporated to yield 4.5 g (85%) of the title compound as an oil.:

MS m/z (relative intensity, 70 eV) 231 (M$^+$, 2), 116 (100), 146 (8).

Step C: N-(5-Nitro-indan-2-yl)-N-propylpropionamide (34, Chart D) and N-(4-Nitro-indan-2-yl)-N-propylpropionamide (33, Chart D).

To an ice-cooled solution of N-indan-2-yl-N-propyl-propionamide (4.5 g, 19.4 mmol) in nitromethane was added "nitrating acid" (20.2 mL, see previous nitrations). The mixture was then stirred at ambient temperature overnight. Ice water was added and the mixture was extracted three times (diethyl ether). The combined organic phases were dried (magnesium sulfate), filtered and evaporated to yield a residue (5.34 g, 99%) containing the two regioisomers. This material was used directly in the next step without separation of the isomers.:

Step D: N-(5-Amino-indan-2-yl)-N-propylpropionamide (36, Chart D) and N-(4-amino-indan-2-yl)-N-propylpropionamide (35, Chart D).

To a solution of the isomeric mixture of (N-(4-and-5-Nitro-indan-2-yl)-N-propylpropionamides, 5.3 g, 19.3 mmol) ammonium formate (33 g) was added under inert atmosphere Pd/C (1.3 g). The mixture was stirred at ambient temperature overnight and then filtered through a Celite-pad. The solution was evaporated and redissolved in water/ diethyl ether. The aqueous phase were extracted two additional times with diethyl ether. The combined organic phases was dried (magnesium sulfate), filtered and evaporated to yield a residue of 3.6 g (76%) containing the two isomers. The isomers were separated on silica using diethyl ether as eluant giving 3.0 g of N-(5-amino-indan-2-yl)-N-propylpropionamide and 0.5 g of N-(4-Amino-indan-2-yl)-N-propylpropionamide.:

(36, Chart D) H NMR (300 MHz, CDCl$_3$) δ 0.82 (t, 3H), 1.15 (t, 3H), 1.55 (sept, 2H), 2.4 (two q, 2H), 2.9 (m, 4H), 3.15 (m, 2H), 3.6 (br s, 2H), 4.65 (q, 0.6H), 5.18 (q, 0.4H), 6.5 (m, 2H), 6.95 (m, 1H); $^{13}$C NMR (75.4 MHz, CDCl$_3$) δ 9.6, 11.2, 11.4, 22.2, 24.0, 26.7, 26.9, 35.6, 36.0, 36.6, 37.0, 44.2, 46.7, 55.4, 57.8, 111.0, 111.1, 113.6, 113.8, 124.7, 124.9, 129.8, 130.9, 141.4, 142.3, 145.2, 145.5, 173.3, 173.8; MS m/z (relative intensity, 70 eV) 246 (M$^+$, 0.2), 131 (100).

(35, Chart D). $^1$H NMR (300 MHz, CDCl$_3$) δ 0.825 (t, 3H), 1.15 (t, 3H), 1.60 (sept, 2H), 2.4 (two q, 2H), 2.7-3.3 (m:s, 6H), 3.6 (br s, 2H), 4.75 (q, 0.5H), 5.20 (q, 0.5H), 6.5 (t, 1H), 6.64 (d, 1H); $^{13}$C NMR (75.4 MHz, CDCl$_3$) δ 9.6, 11.2, 11.5, 22.2, 23.9, 26.8, 27.0, 33.3, 33.4, 36.7, 37.1, 44.3, 47.0, 55.1, 57.4, 112.6, 112.9, 114.4, 124.6, 125.7, 127.6, 128.0, 141.4, 142.3, 142.4, 173.3, 173.9; MS m/z (relative intensity, 70 eV) 246 (M$^+$, 0.2), 131 (100).

Step E: N,N-Dipropyl-indan-2,5-diamine (6g, Chart D, Chart 2).

A solution of N-(5-amino-indan-2-yl)-N-propylpropionamide (2.6 g, 10.5 mmol) in dry diethyl ether (50 mL) was added to a slurry of lithiumaluminum hydride (1.0 g, 26 mmol) in diethyl ether (150 mL) at ambient temperature. After stirring for 1.5 hours water (1.0 mL) followed by 15% sodium hydroxide (1.0 mL) and water (3.0 mL). After stirring for 10 minutes, the inorganic material was filtered off and the resulting solution was evaporated to yield 2.2 g (90%) of the desired product as an oil.:

MS m/z (relative intensity, 70 eV) 232 (M$^+$, 18), 132 (100), 203 (95), 117 (12).

Step F: 6-Dipropyl-amino-1,5,6,7-tetrahydro-1-aza-s-indacene-2,3-dione (8f, Chart 2) and 7-dipropyl-amino-3,6, 7,8-tetrahydro-1-aza-as-indacene-1,2-dione (7f, Chart 2).

N,N-Dipropyl-indan-2,5-diamine was converted into its HCl-salt (giving 2.87 g, 9.5 mmol) and then dissolved in water (39 mL). Chloralhydrate (1.72 g, 10.3 mmol), hydroxylamine hydrochloride (2.08, 30 mmol) and anhydrous sodium sulfate (10.5 g) was added. The mixture was refluxed for 1 hour. After cooling, diluted ammonia was added for basification. The aqueous mixture was extracted with ethyl acetate three times, dried (magnesium sulfate), filtered and evaporated. This material was cooled and to it was added cooled "wet sulfuric acid" (65 mL of water/conc sulfuric acid 1:9). The resulting mixture was stirred 0.5 hour at ambient temperatue and then heated at 80° C. for 1 hour. After cooling, the mixture was poured on ice and basified using conc aqueous ammonia. The aqueous phase was extracted several times with ethyl acetate and the resulting organic phase was dried (magnesium sulfate), filtered and evaporated to yield 2.47 g (93%) of the isomeric mixture.

EXAMPLE 41

Dipropyl-(1,5,6,7-tetrahydro-1-aza-s-indacen-6-yl) amine (11e, Chart 2) and Dipropyl-3,6,7,8-tetrahydro-3-aza-as-indacen-7-yl)amine (9j, Chart 2)

The isomeric mixture of 6-dipropyl-amino-1,5,6,7-tetrahydro-1-aza-s-indacene-2,3-dione and 7-dipropylamino-3,6,7,8-tetrahydro-1-aza-as-indacene-1,2-dione (1.38 g, 4.8 mmol) was dissolved in diethyl ether (50 mL) and added dropwise to a slurry of lithium aluminum hydride (1.0 g, 26.4 mmol) in diethyl ether (100 mL). The mixture was stirred at ambient temperature for 1 hour. Water (1.0 mL), followed by 15% sodium hydroxide (1.0 mL) and water (3.0 mL) was added cautiously and the mixture was stirred for 10 minutes. The solid material was filtered off and the organic solution was evaporated to yield a residue (1.17 g, 95%) containing the two regioisomers. This material was subjected to silica column chromatography and eluted with diisopropyl ether/ethanol (96:4). This material was subjected to silica column chromatography and eluted with diisopropyl ether/ethanol (96:4). Dipropyl-(3,6,7,8-tetrahydro-3-aza-as-indacen-7-yl)amine (118 mg) was first collected, followed by a mixed fraction (176 mg) and dipropyl-(1,5,6,7-tetrahydro-1-aza-s-indacen-6-yl)amine (535 mg) giving a total recovery of 829 mg (67%).:

(11e, Chart 2) m.p. 110°–112° (free base); $^1$H NMR (300 MHz, CDCl$_3$) δ 0.90 (t, 4H), 1.50 (sxt, 4H), 2.52 (t, 4H), 2.9 (m, 2H), 3.1 (two d, 2H), 3.7 (m, 1H), 6.44 (m, 1H), 7.10 (m, 1H), 7.18 (s.1), 7.40 (s, 1H), 8.06 (br s, 1H); $^{13}$C NMR (75.4 MHz, CDCl$_3$) δ 12.1, 20.0, 36.5, 37.0, 53.6, 64.2, 102.2, 106.5, 115.6, 123.5, 127.0, 134.0, 135.3, 136.7;

MS m/z (relative intensity, 70 eV) 256 (M$^+$, 19), 227 (100), 156 (89), 129 (19).

(9j, Chart 2). m.p. 105°–107° (free base); $^1$H NMR (300 MHz, CDCl$_3$) δ 0.94 (t, 6)H, 1.58 (sxt, 4H), 2.58 (t, 4H), 3.1 (m, 3H), 3.3 (two d, 1H), 3.9 (pent, 1H), 6.44 (m, 1H), 7.05 (d, J=8.1 Hz, 1H), 7.2 (m.2), 8.5 (br s, 1H); MS m/z (relative intensity, 70 eV) 256 (M$^+$, 20), 227 (100), 156 (78), 129 (17).

EXAMPLE 42

6-Dipropylamino-1,5,6,7-tetrahydro-1-aza-s-indacen-3-carbaldehyde (12e, Chart 2)

A solution of dipropyl-(1,5,6,7-tetrahydro-1-aza-s-indacen-6-yl)amine (100 mg, 0.39 mmol) in dimethyl formamide (5 mL) was added to a solution of phosphorous oxychloride (200 µL, 329 mg, 2.14 mmol) in dimethyl formamide (5 mL) at –5° C. The mixture was heated at 50° C for 2 hours, poured on ice and treated with 5M sodium hydroxide and heated again for 20 minutes. After cooling, the mixture was extracted using dichloromethane. The combined organic extracts were dried (magnesium sulfate), filtered and evaporated to yield a residue of 70 mg, which was purified on silica using methanol as eluant, yielding 33 mg (30%) of the pure compound as an oil.:

$^1$H NMR (300 MHz, CDCl$_3$) δ 0.90 (t, 6H), 1.5 (m, 4H), 2.55 (t, 2H), 2.8–3.3 (m:s, 4H), 3.65 (m, 1H), 7.20 (s, 1H), 7.75 (s, 1H), 8.1 (s, 1H), 9.55 (s, 1H), 10.0 (s, 1H);

$^{13}$C NMR (75.4 MHz, CDCl$_3$) δ 12.0, 19.9, 36.4, 37.1, 53.4, 107.2, 117.0, 119.3, 135.4, 119.3, 123.5, 135.4, 136.3, 137.4, 139.0, 185.2; MS m/z (relative intensity, 70 eV) 284 (M$^+$, 11), 255 (100), 184 (40), 156 (18).

EXAMPLE 43

1-(6-Dipropylamino-1,5,6,7-tetrahydro-1-aza-s-indacen-3-yl)propan-1-one (12f, Chart 2)

A solution of dipropyl-(1,5,6,7-tetrahydro-1-aza-s-indacen-6-yl)amine (53 mg, 0.21 mmol) in N,N-dimethylpropionamide (200 µL) treated with phosphorous oxychloride (41 µL, 66 mg, 0.44 mmol) and thereafter heated at 80° C. for 2 hours. After cooling 3M sodium hydroxide (7 mL) was added. The resulting mixture was heated again at 80° C. for 15 minutes and then cooled. This aqueous mixture was extracted with ethyl acetate three times. The combined organic extracts was dried (magnesium sulfate), filtered and evaporated to yield a residue, which was repeatedly redissolved in 99% ethanol and evaporated until the residue showed a constant weight of 65 mg (99%) of the desired compound.:

MS m/z (relative intensity, 70 eV) 326 (M$^+$, 42), 226 (100), 207 (43), 170 (25), 196 (20).

EXAMPLE 44

(6-Dipropylamino-1,5,6,7-tetrahydro-1-aza-s-indacen-3-yl)-phenyl methanone (12 g, Chart 2).

A mixture of dipropyl-(1,5,6,7-tetrahydro-1-aza-s-indacen-6-yl)amine (31 mg, 0.12 mmol) N,N-dimethylbenzamide (36 mg, 0.24 mmol) and phosphorous oxychloride (14 µL, 23 mg, 0.15 mmol) was heated at 85° C. overnight. After cooling, 3M sodium hydroxide (4 mL) was added and the resulting mixture was heated at 85° C. for 1 hour. The mixture was cooled and extracted (ethyl acetate) three times. The organic solution was dried (magnesium sulfate), filtered and evaporated to yield 46 mg (100%) of the desired material.: MS m/z (relative intensity, 70 eV) 360 (M$^+$, 12), 331 (100), 105 (38), 260 (31).

EXAMPLE 45

7-Dipropylamino-1,6,7,8-tetrahydro-1-aza-as-indacene-2,3-dione (2c, Chart 1)

Step A: N,N-Dipropyl-indan-2,4-diamine (1a, Chart 1, Chart D).

A solution of N-(4-amino-indan-2-yl)-N-propylpropionamide (0.5 g, 2.0 mmol) in dry diethyl ether (10 mL) was added to a slurry of lithium aluminum hydride (0.2 g, 5.4 mmol) in diethyl ether (50 mL) at ambient temperature. After stirring for 1.5 hours water (0.2 mL) followed by 15% sodium hydroxide (0.2 mL) and water (0.6 mL). After stirring for 10 minutes, the inorganic material was filtered off and the resulting solution was evaporated to yield 0.42 g (90%) of the desired product as an oil.:

MS m/z (relative intensity, 70 eV) 232 (M$^+$, 14), 203 (100), 132 (80), 72 (17).

Step B: 7-Dipropylamino-1,6,7,8-tetrahydro-1-aza-as-indacene-2,3-dione (2c, Chart 1).

N,N-Dipropyl-indan-2,4-diamine was converted into its HCL salt (giving 0.52 g, 1.72 mmol) and dissolved in water (7 mL). Chloralhydrate (312 mg, 1.88 mmol), hydroxylamine hydrochloride (378 mg, 5.4 mmol) and anhydrous sodium sulfate (1.91 g) was added. The mixture was refluxed for 1 hour. After cooling, diluted ammonia was added for basification. The aqueous mixture was extracted with ethyl acetate three times, dried (magnesium sulfate), filtered and evaporated. The material was cooled and to it was added cooled "wet sulfuric acid" (12 mL of water/conc sulfuric acid 1:9). The resulting mixture was stirred 0.5 hour at ambient temperature and the heated at 80° C. for 1 hour. After cooling the mixture was poured on ice and basified using concentrated aqueous ammonia. The aqueous phase was extracted several times with ethyl acetate and the resulting organic phase was dried (magnesium sulfate), filtered and evaporated to yield 0.43 g (83%).:

EXAMPLE 46

Dipropyl-(1,6,7,8-tetrahydro-1-aza-as-indacen-7-yl) amine (3c, Chart 1)

7-Dipropylamino-1,6,7,8-tetrahydro-1-aza-as-indacene-2,3-dione (0.42 mg, 1.46 mmol) was dissolved in dry diethyl ether (20 mL) and dropped to a slurry of lithium aluminum hydride (300 mg, 7.9 mmol) in dry diethyl ether (50 mL). The mixture was stirred at ambient temperature for 1 hour. Water (300 µL) followed by 15% sodium hydroxide (300 µL) and water (900 µL) was added and the mixture was stirred for 10 minutes. The solid material was filtered off and the organic solution was evaporated to yield a residue of 380 mg, which was chromatographed on a silica column using diisopropyl ether/ethanol (96:4) giving 175 mg (47%) of the pure material. The fumaric acid salt was prepared and recrystallized from ethanol.:
m.p. 178°–183° (Fumarate); $^1$H NMR 9300 MHz, CDCl$_3$) δ 0.90 (t, 6H), 1.53 (sxt, 4H), 3.0 (m, 2H), 3.1 (m, 2H), 3.9 (pent, 1H), 6.55 (t, 1H), 6.99 (d, 1H), 7.15 (d, 1H), 7.95 (br s, 1H); $^{13}$C NMR (75.4 MHz, CDCl$_3$) δ 12.0, 20.5, 33.3, 36.5, 53.5, 63.4, 103.2, 116.8, 118.9, 123.2, 123.3, 126.5, 132.7, 136.1; MS m/z (relative intensity, 70 eV) 256 (M$^+$, 22), 227 (100), 156 (68), 129 (14).

EXAMPLE 47

Benzyl-propyl-(1,5,6,7-tetrahydro-1-aza-s-indacen-6-yl)amine (11f, Chart 2) and Benzyl-propyl-(3,6,7,8-tetrahydro-3-aza-as-indacen-7-yl)amine (9k, Chart 2)

Step A: N-Indan-2-yl-N-propyl-benzamide (39, Chart D).

To a stirred solution of Indan-2-yl-propyl-amine (20.0 g, 114 mmol) in dichloro methane (200 mL) triethyl amine (17.4 mL, 125 mmol) was added. To this solution was then dropwise added benzoyl chloride (17.6 g, 125 mmol), followed by stirring at ambient temperature for 2 hours. The reaction was finally quenched by addition of dilute hydrochloric acid (50 mL, 10% HCl). The organic layer was separated, washed with water and dried over magnesium sulfate. Evaporation of the solvent yielded 31.5 g (99%) of the title compound as a dark oil.:
MS (EI) m/z (relative intensity, 70 eV) 279 (M$^+$, 4), 116 (100), 164 (89), 105 (83), 77 (52), 115 (20), 117 (15), 165 (11).

Step B: N-(5-Nitro-indan-2-yl)-N-propylbenzamide (40, Chart D) and N-(4-Nitro-indan-2-yl)-N-propylbenzamide (41, Chart D).

To an ice-cooled solution of N-indan-2-yl-N-propyl-benzamide (16.5 g, 59 mmol) in nitromethane (250 mL) was gently added dropwise "nitrating acid" (80 m:; 6.6% nitric acid, 80.3% sulfuric acid and 13.1% water). The resulting mixture was stirred for 4 hours and poured on ice water. The mixture was shaken and the organic solution was dried (magnesium sulfate), filtered and evaporated to yield 17.6 g (92%) of a mixture containing the two isomers, N-(5-nitro-indan-2-yl)-N-propylbenzamide and N-(4-nitro-indan-2-yl)-N-propylbenzamide in a 5:1 relationship.:
(40, Chart D) MS m/z (relative intensity, 70 eV) 324 (M$^+$, 17), 105 (100), 77 (47), 164 (43), 134 (29).
(41, Chart D) MS m/z (relative intensity, 70 eV) 324 (M$^+$, 5), 105 (100), 307 (49), 77 (47), 134 (31) 164 (23).

Step C: N-(5-Amino-indan-2-yl)-N-propylbenzamide (42, Chart D) and N-(4-Amino-indan-2-yl)-N-propylbenzamide (43, Chart D).

The isomeric mixture containing N-(5-Nitro-indan-2-yl)-N-propylbenzamide and N-(4-Nitro-indan-2-yl)-N-propylbenzamide (17.3 g, 53 mmol) was mixed with ammonium formate (30 g, 470 mmol) in ethanol (300 mL). Under an inert atmosphere was added 2.5 g Pd/C and the reaction mixture was stirred at ambient temperature overnight and then filtered through a Celite-pad. The solution was evaporated and redissolved in diethyl ether/water, shaken and the aqueous phase was extracted two additional times. The combined organic phases was dried (magnesium sulfate), filtered and evaporated to yield a residue of 15 g containing the two isomers. This material was roughly purified on silica gel column using diethyl ether as eluant giving 9.1 g (58%) of the two isomers. Of this material 4.3 g were further chromatographed in silica using diethyl ether/hexane (3:1) as eluant, which yielded 3.1 g of N-(5-nitro-indan-2-yl)-N-propylbenzamide and 1.3 g of a mixture of both isomers.:
MS m/z (relative intensity, 70 eV) 294 (M$^+$, 0.1), 131 (100), 77 (18), 105 (16).

Step D: N-Benzyl-N-propyl-indan-2,5-diamine (63, Chart 2, Chart D).

A solution of N-(5-amino-indan-2-yl)-N-propylbenzamide (3.0 g, 10.2 mmol) in diethyl ether (50 mL) was added to a slurry of lithium aluminum hydride (1.4, 36.9 mmol) in diethyl ether (60 mL). After stirring overnight, water (. 14 mL), 15% sodium hydroxide (1.4 mL) and water (4.2 mL) was added in consecutive order. The mixture was stirred for 0.5 hour and then filtered through a Celite pad. Subsequent evaporation yielded 2.60 g (91%) of the desired material.:
$^1$H NMR (300 MHz, CDCl$_3$) δ 0.86 (t, 3H), 1.50 (sxt, 2H), 2.48 (t, 2H), 2.8–3.05 (m:s, 4H), 3.52 (br s, 2H), 3.65 (s, 2H), 3.72 (pent, 1H), 6.50 (d, J–7.9 Hz, 1H), 6.56 (s, 1H), 6.97 (d, J=7.9 Hz, 1H), 7.2–7.5 (m, 5H); $^{13}$C NMR (75.4 MHz, CDCl$_3$) δ 11.8, 20.0, 34.9, 36.0, 52.9, 55.3, 62.3, 111.3, 113.4, 124.8, 126.5, 128.0, 128.5, 132.0, 140.6, 143.2, 144.8; MS m/z (relative intensity, 70 eV) 280 (M$^+$, 21), 251 (100), 91 (48), 132 (42), 222 (22), 120 (17).

Step E: 6-(Benzyl-propyl-amino)-1,5,6,7-tetrahydro-1-aza-s-indacene-2,3-dione (8 g, Chart 2) and 7-(Benzyl-propyl-amino)-3,6,7,8-tetrahydro-1-aza-as-indacene-1,2-dione (7 g, Chart 2).

A mixture of N-benzyl-N-propyl-indan-2,5-diamine hydrochloride (3.5 g, 9.9 mmol), chloral hydrate (1.8 g, 11 mmol), hydroxylamine hydrochloride (2.2 g, 32 mmol) and dry sodium sulfate (11 g) was refluxed for 1.5 hours. After cooling the mixture was basified using diluted ammonia. The resulting mixture was extracted (ethyl acetate), dried (magnesium sulfate), filtered and evaporated to a residue of 3.9 g. This material was cooled and treated with a cooled solution of water (7 ml) in conc. sulfuric acid (63 mL). The resulting mixture was heated at 80° C. for 45 min. After cooling, the mixture was poured on ice and basified using conc. ammonia in water. Extraction (ethyl acetate), drying (magnesium sulfate), filtering and evaporation yielded 3.17 g (96%) of the desired regioisomers:

Step F:
The isomeric mixture of 6-(benzyl-propyl-amino)-1,5,6, 7-tetrahydro-1-aza-s-indacene-2,3-dione and 7-(Benzyl-propyl-amino)-3,6,7,8-tetrahydro-1-aza-as-indacene-1,2-dione (3.17 g, 9.5 mmol) in dry diethyl ether (50 mL) was added dropwise over a period of 20 min to a slurry of lithium aluminum hydride in dry diethyl ether (150 mL) and stirred over night at ambient temperature. Water (2 mL) followed by 15% sodium hydroxide (2 mL) and water (6 mL) was added and the mixture was stirred for 2 hrs. The solid material was filtered off and the organic solution was evaporated to yield a residue of 2.75 g. This material was subjected to silica column chromatography, eluating with hexane fraction/diethyl ether (3:1). Pure benzyl-propyl-(3,6,7,8-tetrahydro-3-aza-as-indacen-7-yl)amine (250 mg) followed by a mixed fraction (110 mg) and benzyl-propyl-(1,5,6,7-tetrahydro-1-aza-s-indacen-6-yl)amine (920 mg) was collected as oils giving a total recover of 1.28 g (44 %):

(11f, Chart 2) $^1$H NMR (300 MHz, CDCl$_3$) δ 0.85 (t, 6H), 1.51 (sxt, 4H), 2.50 (t, 4H), 2.95–3.2 (m, 4H), 3.70 (s, 2H), 3.75 (pent, 1H), 6.55 (m, 1H), 7.10 (t, 1H), 7.15–7.45 (m, 7H), 8.0 (br s, 1H); $^{13}$C NMR (75.4 MHz, CDCl$_3$) δ 11.9, 20.0, 35.7 36.2, 53.1, 55.5, 63.1, 102.2, 106.5, 115.6, 123.5, 126.5, 127.0, 128.1, 128.6, 134.1, 135.3, 136.8, 140.8; MS m/z (relative intensity, 70 eV) 304 (M⁺, 26), 275 (100), 156 (39), 246 (31), 91 (32).

(9k, Chart 2). ¹H NMR (300 MHz, CDCl₃) δ 0.90 (t, 6H), 1.56 (sxt, 4H), 2.56 (t, 4H), 3.05–3.35 (m, 4H), 3.70 (s, 2H), 3.95 (pent, 1H), 6.48 (s, 1H), 7.06 (d, J=8.3 Hz, 1H), 7.15–7.50 (m, 7H), 8.18 (br s, 1H); ¹³C NMR (75.4 MHz, CDCl₃) δ 12.0, 20.3, 34.4, 36.0, 53.0, 55.4, 62.3, 100.6, 109.2, 118.6, 124.2, 124.7, 126.6, 128.1, 128.6, 132.7, 133.2, 135.0, 140.8; MS m/z (relative intentity, 70 eV) 304 (M⁺, 22), 275 (100), 156 (40), 207 (37), 246 (31), 91 (30).

EXAMPLE 48

Propyl-(1,5,6,7-tetrahydro-1-aza-s-indacen-6-yl)-amine (11g, Chart 2

To a solution of benzyl-propyl-(3,6,7,8-tetrahydro-3-aza-as-indacen-7-yl)amine (9k, Chaart 2) (0.87 g, 2.86 mmol) in ethanol (50 mL) was added Pd/C (0.5 g, inert atmosphere) and ammonium formate (1.5 g, 24 mmol). The mixture was heated at 50° C. for 30 min., cooled and filtered through a Celite-pad. The organic solution was evaporated and the residue dissolved in water and basified (10% sodium carbonate). Extraction with diethyl ether, drying (magnesium sulfate), filtering, and evaporation yielded 0.45 g (74%) of the title compound.

¹H NMR (300 MHz, CDCl₃) δ 0.95 (t, 3H), 1.4 (br s, 1H), 1.55 (sxt, 2H), 2.67 (t, 2H), 2.83 (m, 2H), 3.25 (m, 2H), 3.65 (pent, 1H), 6.45 (m, 1H), 7.11 (m, 1H), 7.18 (s, 1H), 7.43 (s, 1H), 8.3 (br s, 1H); ¹³C NMR (75.4 MHz, CDCl₃) δ 11.9, 23.5, 39.5, 40.0, 50.2, 60.6, 102.1, 106.8, 115.9, 123.6, 127.1, 133.8, 135.4, 136.4; MS m/z (relative intensity, 70 eV) 214 (M⁺, 100), 145 (97), 156 (91), 185 (77), 155 (71), 130 (59).

EXAMPLE 49

Cyclopropylmethyl-propyl-(1,5,6,7-tetrahydro-1-aza-s-indacen 6-yl)-amine (11h, Chart 2)

Step A: Cyclopropanecarboxylic acid propyl-(1,5,6,7-tetrahydro-1-aza-s-ubdaceb-6-yl)-amide.

To a stirred solution of propyl-(1,5,6,7-tetrahydro-1-aza-s-indacen-6-yl)-amine (11g, Chart 2) (75 mg, 0.35 mmol) in dichloromethane (5 mL) was added triethylamine (0.1 mL), followed by the addition of cyclopropanecarbonyl chloride (40 μL, 46 mg. 0.44 mmol). The mixture was stirred at ambient temperature for 2 hrs. The reaction was quenched by the addition of 10% aqueous sodium carbonate and the mixture stirred. The organic phase was washed with dilute hydrochloric acid, dried (megnesium sulfate and concentrated to yield 100 mg(100%) of the desired compound.

Step B: Cyclopropylmethyl-propyl-(1,5,6,7-tetrahydro-1-aza-s-indacen-6-yl)-amide (100 mg, 0.35 mmol) in dry diethyl ether was added in small potions lithium aluminum hydride (90 mg, 2.37 mmol). The reaction mixture was stirred over night and then quenched by the consecutive addition of water (90 μL), 15% sodium hydroxide (90 μL) and water (270 μL). After stirring for 15 min., the solid material was filtered off and the solvent removed in vacuo to yield a residue of 78 mg (83%) of the title compound.

MA m/z (relative intensity, 70 eV) 268 (M⁺, 30), 239 (100), 156 (42), 155 (23), 210 (20) 192 (9).

EXAMPLE 50

1-[6-(Cyclopropylmethyl-propyl-amino)-1,5,6,7-tetrahydro-1-aza-s-indacen-3-yl]-propan-1-one (12h, Chart 2)

To a solution of cyclopropylmethyl-propyl-(1,5,6,7-tetrahydro-a-aza-s-indacen-6-yl)amine (11h, Chart 2) (62 mg, 0.23 mmol) in N,N-dimethyl propionamide (200 μL) was added phosphorous oxychloride (40 μL, 66 mg, 0.43 mmol). The mixture was heated at 80° C. for 1 hr. Then 15% sodium hydroxide (7mL) was added and the mixture was heated for an additional 15 min. After cooling, the aqueous mixture was extracted with ethyl acette. The organic extrace was dried (magnesium sulfate) and concentrated to yield 74 mg (100%) of the desired material.

MS m/z (relative intensity, 70 eV) 324 (M⁺, 20), 295 (100), 212 (24), 253 (16), 182 (15), 154 (9).

EXAMPLE 51

Cyclopropylmethyl-propyl-(3-propyl-1,5,6,7-tetrahydro-1-aza-s-indacen-6-yl)-amine (12i, Chart 2)

To a stirred solution of 1-[6-(cyclopropylmethyl-propyl-amino)-1,5,6,7-tetrahydro-1-aza-s-indacen-3-yl]-propan-1-one (12h, Chart 2) (58 mg, 0.18 mmol) in dry diethyl ether (4 mL) was added in small portions lithium aluminum hydride (40 mg, 1.06 mmol). The reaction mixture was stirred over night and then quenched by the consecutive addition of water (40 μL), 15% sodium hydroxide (40 μL) and water (120 μL). After stirring for 15 min., the solid material was filtered off and the solvent removed in vacuo to yield a residue of 28 mg (50%) of the title compound.

MS m/z (relative intensity, 70 eV) 310 (M⁺, 27), 281 (100), 198 (33), 168 (219), 252 (15), 155 (8).

EXAMPLE 52

[2-(4-Fluoro-phenyl)-ethyl]-propyll-(1,5,6,7-tetrahydro-1-aza-s-indacen-6-yl)-amine (11i, Chart 2)

To a stirred solution of propyl-(1,5,6,7-tetrahydro-1-aza-s-indacen-6-yl)amine (11 g, Chart 2) (90 mg, 0.42 mmol) in dichloromethane (5 mL) was added triethylamine (0.1 mL), followed by the addition of 4-fluoro-phenyl-acetyl chloride (75 mg, 0.43 mmol). The mixture was stirred at ambient temperature for 2 hrs. The reaction was quenched by the addition of 10% aqueous sodium carbonate and the mixture stirred. The organic phase was washed with dilute hydrochloric acid, dried (magnesium sulfate and concentrated to yield 140 mg (96%) of the desired compound.

MS m/z (relative intensity, 70 eV) 348 (M⁺, 0.2), 155 (100), 109 (8), 129 (3).

Step B: [2-(4-Fluoro-phenyl)-ethyl]-propyl-(1,5,6,7-tetrahydro-1-aza-s-indacen-6-yl)-amine ((11i, Chart 2).

To a stirred solution of 2-(4-fluoro-phenyl)-ethyl]-propyl-(1,5,6, 7-tetrahydro-1-aza-s-indacen-6-yl)-acetamide (140 mg, 0.40 mmol) in dry diethyl ether (4 mL) was added in small portions lithium aluminum hydride (150 mg, 3.95 mmol). The reaction mixture was stirred for 2 hrs. and then quenched by the consecutive addition of water (150 μL), 15% sodium hydroxide (150 μL) and water (450 μL). After stirring for 15 min., the solid material was filtered off and the solvent removed in vacuo to yield a residue of 108 mg (81%) of the title compound.

MS m/z (relative intensity, 70 eV) 334 (M⁺, 2), 227 (100), 156 (58), 228 (17), 155 (16), 129 (13).

EXAMPLE 53

N,N-Diethyl-2-(6-{[2-(4-fluoro-phenyl)ethyl] propylamino}-1,5,6,7-tetrahydro-1-aza-s-indacen-3-yl)-2-oxo-acetamide (12j, Chart 2)

An ice-cooled solution of [2-(4-fluoro-phenyl)-ethyl]-propyl-(1,5,6,7-tetrahydro-1-aza-s-indacen-6-yl)-amine (11i, Chart 2) (100 mg, 0.30 mmol) in dry diethyl ether (1 mL) was treated dropwise with oxalyl chloride (76 µL, 110 mg, 0.87 mmol). A precipitate was formed and more diethyl ether (1 mL) was added to facilitate stirring, which was continued for 0.5 hr. Then, a solution of diethyl amine (300 µL, 218 mg, 3.0 mmol) in dry diethyl ether (0.5 mL) was added. Stirring at ambient temperature was continued for 2 hrs. Finally, saturated sodium hydrogen carbonate was added and the organic layer separated. The aqueous layer was extracted with ethyl acetate. The combined organic phases were dried (magnesium sulfate), filtered and evaporated to yield a residue (67 mg) of crude material consisting mainly of the title compound.

MS m/z (relative intensity, 70 eV) 461 ($M^+$, 2), 354 (100), 283 (28), 182 (26), 355 (25), 154 (13), 72 (10).

Preparation 1 trans-4-Benzyl-2,3,4,5,6,7,10,17-octahydro-1H-4,17-diaza-cyclopenta[a]phenanthrene-16-carboxylic acid methyl ester (54 Chart E).

Step A: trans-Trifluoro-methanesulfonicacid 4-benzyl-1,2,3,4,4a,5,6,10b-octahydro-benzo[[f]quinolin-7-yl ester (44, Chart E).

A solution of trans-7-hydroxy-4-benzyl-1,2,3,4,4a,5,6,10b-octahydro-benzo[f]quinoline (3.3 g, 13.47 mmol, (for preparation see Wikström et al., *J. Med. Chem.*, 1982, 25, 925–931), triethyl amine (2.04 g, 20.2 mmol) in 300 mL of dichloromethane was cooled to −30° C. Then triflic anhydride (5.7 g, 20.2 mmol) in 30 mL of dichloromethane was added dropwise. The reaction mixture was allowed to reach room temperature and was then stirred for 2 hrs at 25° C. The reaction mixture was quenched with cold water, the organic layer separated and washed with 2 portions of cold 5% HCl-solution. Following a wash of the organic portion with brine and drying (magnesium sulfate), the solvent was removed under reduced pressure and the residue was chromatographed on a silica column with methanol:dichloromethane (1:19 (v/v)) as eluant. The solvents from the collected fractions containing pure 44 were evaporated yielding a pale oil 4.87 g (85%).

MS m/z (relative intensity, 70 eV) 425 ($M^+$, 42), 292 (78), 264 (21), 91 (100).

Step B: trans-4-benzyl-1,2,3,4,4a,5,6,10b-octahydro-benzo[f]quinolin-7-carboxylic acid methyl ester (46 Chart E).

A mixture of compound trans-trifluoro-methanesulfonic acid 4-benzyl-1,2,3,4,4a,5,6,10b-octahydro-benzo[f]quinolin-7-yl ester (3.1 g, 7.3 mmol), triethyl amine (2 ml, 14.6 mmol), pethanol (12.3 ml, 0.28 tool), palladium acetate (50 mg, 0.22 mmol), 1.3-bis-(diphenylphosphino)propane (90 mg, 0.22 mmol) in dimethyl sulfoxide (25 mL) was stirred at room temperature for 15 min or until all particles were dissolved (Dolle et al., *J. Chem. Soc. Chem. Commun.*, 1987, 904–905). A stream of CO9 g) was passed through the solution for 4–5 min. and then the reaction vessel was placed under a slightly positive pressure of carbon monoxide (g) (1 atm.). The temperature was increased to 70° C. (oil bath). After 6 h GC analysis revealed a complete absence of the starting triflate and indicated trans-4-benzyl-1,2,3,4,4a,5,6,10b-octahydro-benzo[f]quinolin-7-carboxylic acid methyl ester as the major product. The reaction mixture was allowed to cool to room temperature. Water (200 mL) was then added and the aqueous solution was extracted with 5 portions of diethyl ether. The combined organic phases were washed with water until neutral, dried (magnesium sulfate) and evaporated. The residue was chromatographed on a silica column using methanol:dichloromethane (1:19 (v/v)) as eluant. The solvents from the collected fractions containing pure 46 were evaporated yielding 1.9 g (78%).

MS m/z (relative intensity, 70 eV) 335 ($M^+$ 100), 258 (20), 244 (23), 91 (50).

Step C: trans-(4-Benzyl-1,2,3,4,4a,5,6,10b-octahydro-benzo[f]quinolin-7-yl)-methanol (48 Chart E).

A solution of trans-4-benzyl-1,2,3,4,4a,5,6,10b-octahydro-benzo[f]quinolin-7-carboxylic acid methyl ester (1.9 g, 5.67 mmol) in 50 mL of dry diethyl ether was cooled to 0° C. Solid lithium aluminum hydride (1.5 g, 39.5 mmol) was then added in small portions. The mixture was stirred for 1 hour at 0° C. The reaction was then terminated by the addition of water (1 mL), 15% sodium hydroxide solution (1 mL) and finally water (3 mL). The resulting mixture was filtered through a pad of Celite, dried (magnesium sulfate) and evaporated to dryness. The residue was chromatographed on a silica column with methanol:dichloromethane (1:19 (v/v)) as eluant. The solvents from the collected fractions containing pure 48 were evaporated yielding 1.5 g (86%) as an oil.

MS m/z (relative intensity, 70 eV) 307 ($M^+$ 100), 230 (10), 158 (15), 91 (47).

Step D: trans-4-Benzyl-1,2,3,4,4a,5,6,10b-octahydro-benzo[f]quinolin-7-carbaldehyde (50 Chart E).

To a solution of trans-(4-benzyl-1,2,3,4,4a,5,6,10b-octahydro-benzo[f]-quinolin-7-yl-methanol (1.5 g, 4.88 mmol) in 80 mL of dichloromethane was added pyridinium chlorochromate (1.5 g, 7.44 mmol) in small portions. The mixture was stirred for 1 hr. at room temperature and then quenched with cold 10% sodium carbonate solution (50 ml), the layers separated and the waterphase extracted with 2 portions of dichloromethane (100 ml). The combined organic phases were dried (magnesium sulfate) and the solvent was removed under reduced pressure. The residue was chromatographed on a silica column with methanol:dichloromethane (1:19 (v/v)) as eluant. The solvents from the collected fractions containing pure 50 were evaporated yielding 1.2 g (80%) as an oil.

MS m/z (relative intensity, 70 eV) 305 ($M^+$ 100), 214 (16), 159 (20), 129 (17), 91 (61).

Step E: trans-2-Azidomethyl-3-(4-benzyl-1,2,3,4,4a,5,6,10b-octahydro-benzo[f]quinolin-7-yl)-acrylic acid methyl ester (52 Chart E).

Trans-4-benzyl-1,2,3,4,4a,5,6,10b-octahydro-benzo[f]quinolin-7-carbaldehyde (1.4 g, 4.59 mmol), ethyl azidoacetate (2.7g, 20.9 mmol), diethyl ether (10 ml), and methanol (30 ml) were cooled to −5° C. (Henn et al., *J. Chem. Soc. Perkin Trans. 1*, 1984, 2189–2196). Sodium methoxide (3.89 ml, 18.4 mmol, of a 25% w/w solution in methanol) was slowly added. The reaction was allowed to reach ambient temperature and stirred for 1 hr. The mixture was cooled to 0° C. and saturated aqueous ammonium chloride added. The reaction was rapidly partioned between ether and 10% aqueous sodium carbonate. The ethereal layer was washed with water and brine and the resulting organic phase dried (magnesium sulfate) and evaporated to dryness. The residue was used without any further purifications (1.85 g, 100%).

Step F: trans-4-Benzyl-2,3,4,5,6,7,10,17-octahydro-1H-4,17-diaza-cyclopenta[a]phenanthrene-16-carboxylic acid methyl ester (54 Chart E).

trans-2-Azidomethyl-3-(4-benzyl-1,2,3,4,4a,5,6,10b-octahydro-benzo[f]quinolin-7-yl)-acrylic acid methyl ester (1.85 g) and toluene (30 ml) were brought to reflux for 2 hrs. The solution was cooled and the solvent was evaporated to dryness. Purification of the crude reaction mixture by flash chromatography (toluene:ethyl acetate, 4/1 (v/v)) afforded 0.8 g (46%) of pure 54 as an oil.

MS m/z (relative intensity, 70 eV) 374 ($M^+$ 100), 342 (9), 224 (8), 159 (7), 91 (13).

Preparation 2 cis-4-Benzyl-2,3,4,5,6,7,10,17-octahydro-1H-4,17-diaza-cyclopenta[a]phenanthrene-16-carboxylic acid methyl ester (55 Chart E).

Step A: cis-Trifluoro-methanesulfonic acid 4-benzyl-1,2,3,4,4a,5,6,10b-octahydro-benzo[f]quinolin-7-yl ester (45, Chart E).

This compound was prepared as described for 44 from cis-7-hydroxy-4-benzyl-1,2,3,4,4a,5,6,10b-octahydrobenzo[f]quinoline (6.45 g, 22 mmol, for preparation see Wikström et al., *J. Med. Chem.*, 1982, 25, 925–931). Purification of the crude reaction mixture by flash chromatography (dichloromethane/methanol, 19/1 (v/v)) afforded 7.8 g (83%) of pure 45 as an oil.

MS m/z (relative intensity, 70 eV) 425 ($M^+$ 18), 292 (91), 264 (13), 91 (100).

Step B: cis-4-benzyl-1,2,3,4,4a,5,6,10b-octahydro-benzo[f]quinolin-7-carboxylic acid methyl ester (47 Chart E).

This compound was prepared as described for 46 from cis-trifluoro-methanesulfonic acid 4-benzyl-1,2,3,4,4a,5,6,10b-octahydro-benzo[f]quinolin-7-yl ester (3.7 g, 8.7 mmol). Purification of the crude reaction mixture by flash chromatography (dichloromethane/methanol, 19/1 (v/v)) afforded 2.0 g (69%) of pure 47 as an oil.

MS m/z (relative intensity, 70 eV) 324 ($M^+$ 100), 258 (20), 244 (23), 91 (79).

Step C cis-(4-benzyl-1,2,3,4,4a,5,6,10b-octahydro-benzo[f]quinolin-7-yl)-methanol (49 Chart E)

This compound was prepared as described for 48 from cis-4-benzyl-1,2,3,4,4a,5,6,10b-octahydro-benzo[f]quinolin-7-carboxylic acid methyl ester (1.75 g, 5.22 mmol). Purification of the crude reaction mixture by flash chromatography (dichloromethane/methanol, 19/1 (v/v)) afforded 1.4 g (88%) of pure 49 as an oil;

MS m/z (relative intensity, 70 eV) 307 ($M^+$ 100), 230 (14), 158 (12), 91 (47).

Step D cis-4-benzyl-1,2,3,4,4a,5,6,10b-octahydro-benzo[f]quinolin-7-carbaldehyde (51 Chart E)

This compound was prepared as described for 50 from cis-(4-benzyl-1,2,3,4,4a,5,6,10b-octahydro-benzo[f]quinolin-7-yl)-methanol (1.6 g, 5.21 mmol). Purification of the crude reaction mixture by flash chromatography (dichloromethane/methanol, 19/1 (v/v)) afforded 1.45 g (92%) of pure 51 as an oil;

MS m/z (relative intensity, 70 eV) 305 ($M^+$ 100), 214 (18), 159 (19), 129 (17), 91 (58).

Step E cis-2-Azidomethyl-3-(4-benzyl-1,2,3,4,4a,5,6,10b-octahydro-benzo[f]quinolin-7-yl)-acrylic acid methyl ester (53 Chart E)

This compound was prepared as described for 52 from cis-4-benzyl-1,2,3,4,4a,5,6,10b-octahydro-benzo[f]quinolin-7-carbaldehyde: (1.2 g, 3.93 mmol). The residue was used without further purification (1.56 g, 99%).

Step F cis-4-Benzyl-2,3,4,5,6,7,10,17-octahydro-1H-4,17-diaza-cyclopenta[a]phenanthrene-16-carboxylic acid methyl ester (55 Chart E)

This compound was prepared as described for 54 from cis-2-Azidomethyl-3-(4-benzyl-1,2,3,4,4a,5,6,10b-octahydro-benzo[f]quinolin-7-yl)-acrylic acid methyl ester (1.56 g). The residue was used without further purification (1.35 g, 91%);

MS m/z (relative intensity, 70 eV) 374 (M* 100), 342 (14, 224 (8), 159 (6), 91 (13).

Preparation 3 trans-2,3,4,5,6,7,10,17-Octahydro-1H-4,17-diaza-cyclopenta[a]phenanthrene-16-carboxylic acid methyl ester (56 Chart E)

To a solution of trans-4-benzyl-2,3,4,5,6,7,10,17-octahydro-1H-4,17-diaza-cyclopenta[a]phenanthrene-16-carboxylic acid methyl ester (0.8 g, 2.13 mmol) in methanol (15 ml, plus some few drops of toluene) were added ammonium formate (0.84 g, 8.52 mmol) and Pd/C (125 mg) under an Ar atmosphere. The mixture was refluxed for 1.5 hours and then filtered through a pad of Celite. The solvents were evaporated under reduced pressure and the residue redissolved in dichloromethane (50 ml). The organic mixture was washed several times with 10% aqueous solution of sodium carbonate, dried (magnesium sulfate) and evaporated to dryness (630 mg). The residue was used without further purification:

MS m/z (relative intensity, 70 eV) 284 ($M^+$ 100), 283 (21), 252 (15), 241 (30), 209 (18).

Preparation 4 cis-2,3,4,5,6,7,10,17-octahydro-1H-4,17-diaza-cyclopenta[a]phenanthrene-16-carboxylic acid methyl ester (57 Chart E)

This compound was prepared as described for 56 from cis-4-Benzyl-2,3,4,5,6,7,10,17-octaydro-1H-4, 17-diaza-cyclopenta[a]phenanthrene-16-carboxylic acid methyl ester (0.8 g). The residue was used without furthe rpurification:

MS m/z (relative intensity, 70 eV) 284 ($M^+$ 100), 241 (28), 227 (36), 207 (43), 195 (31).

Preparation 5 trans-4-Propyl-2,3,4,5,6,7,10,17-octahydro-1H-4,17-diaza-cyclopenta[a]phenanthrene-16-carboxylic acid methyl ester (58 Chart E)

A mixture of trans-2,3,4,5,6,7,10,17-Octahydro-1H-4,17-diaza-cyclopenta[a]phenanthrene-16-carboxylic acid methyl ester (0.63 g), propionaldehyde (0.28 ml) and acetic acid (0.2 ml) were dissolved in tetrahydrofuran (30 ml). To the mixture, sodium triacetoxy borohydride (0.74 g) was added in one portion, and the resulting suspension was stirred at room tempeorature for 12 hours. The mixture was then evaporated to dryness, redissolved in dichloromethane (50 ml) and washed several times with 10% aqueous solution of sodium carbonate. The organic phase was dried (magnesium sulfate), filtered and evaporated to dryness. Purification of the crude reaction mixture by flash chromatography (dichloromethane/methanol, 12/1 (v/v)) afforded 0.5 g (69%, based on 54) of pure 58 as an oil;

$^1$H NMR (300 MHz, CDCl$_3$) δ 0.9 (t. 6H), 1.2 (m, 1H), 1.5–1.8 (m, 4H), 2.2–3.2 (m, 9H), 3.95 (s, 3H), 7.2–7.3 (m, 3H), 9.1 (s, 1H); MS m/z (relative intensity, 70 eV) 326 ($M^+$ 35), 297 (100), 265 (16), 133 (17), 84 (29); Analysis calc'd for $C_{20}H_{26}N_2O_2x$ 0.25 H$_2$O: C, 72.6; H, 8.1; N, 8.5; found: C, 72.1; H, 7.6; N, 8.0.

Preparation 6 cis-4-Propyl-2,3,4,5,6,7,10,17-octahydro-1H-4,17-diaza-cyclopenta[a]phenanthrene-16-carboxylic acid methyl ester (59, Chart E)

This compound was prepared as described for 58 from cis-2,3,4,5,6,7,10,17-octahydro-1H-4,17-diaza-cyclopenta[a]phenanthrene-16-carboxylic acid methyl ester (0.47 g):

MS m/z (relative intensity, 70 eV) 326 ($M^+$ 33), 298 (22), 297 (100), 265 (14), 133 (10), 84 (19).

Preparation 7 trans-4-Propyl-2,3,4,5,6,7,10,17-octahydro-1H-4,17-diaza-cyclopenta[a]phenanthrene (60, Chart E).

To a solution of trans-4-propyl-2,3,4,5,6,7,10,17-octahydro-1H-4,17-diaza-cyclopenta-[a]phenanthrene-16-carboxylic acid methyl ester (180 mg, 0.55 mmol) in methanol (3 ml) was added 3N sodium hydroxide (2 ml). The mixture was brought to reflux for 2 hours and then acidified (pH≈2) with 10% aqueous solution of hydrochloric acid. The solvent was removed and azeotroped with absolute ethanol in vacuo. The remaining residue was redissolved in pyridine (5 ml) and refluxed for 2 hours and then cooled. The solution was evaporated to yield a residue (150 mg) containing the title compound and the corresponding carboxylic acid;

MS m/z (relative intensity, 70 eV) 268 ($M^+$ 42), 240 (19.7), 239 (100), 168 (11), 84 (32)

TABLE 1

Effects on DOPA and 5-HTP accumulation in reserpine - pretreated rats. Also shown are the in vitro affinities for brain dopamine (D2, Spiperone) and serotonin (5-HT1A, 8-OH-DPAT) receptor sites in non-pretreated rats.

| Example | DOPA ED50 (μmol/kg, sc.) | | 5-HTP ED50 (μmol/kg, sc.) | In vitro binding Ki nM | |
|---|---|---|---|---|---|
| | Stri. | Cortex. | Limbic | D2-spip. | 5HT1A |
| 1 | P(78%, 50) | I(50) | I(50) | 3520* | 9930 |
| 2 | P(48%, 50) | I(50) | P(61%, 50) | 320 | 1120 |
| 4 | I(50) | I(50) | 5.8 | 15900 | 25300 |
| 5 | P(26%, 3.1) | I(50) | P(62%, 50) | 270 | 178 |
| 7A** | 0.3 | I(12.5) | P(72%, 3.1) | 50 | 500 |
| 7A(−)** | P(31%, 25) | P(73%, 25) | P(68%, 25) | 257 | 1453 |
| 7A(+)** | 0.12 | P(67%, 12.5) | P(80%, 12.5) | 35 | NT |
| 7 | P(48%, 50) | I(50) | I(50) | 4200 | 340 |
| 8 | 0.015 | P(57%, 0.2) | I(50) | 16 | 2600 |
| 8(+) | P(60%, 0.2) | I(0.2) | I(0.2) | NT | NT |
| 9 | P(37%, 12.5) | P(85%, 12.5) | I(12.5) | 278* | NT |
| 10 | 0.004 | P(79%, 3.1) | I(3.1) | 10.1* | NT |
| 16 | P(36%, 50) | I(50) | P(50) | 924* | NT |
| 17 | 1.0 | P(79%, 33.3) | I(33.3) | 205* | NT |
| 15 | P(35%, 50) | P(88%, 50) | P(52%, 50) | 164* | 124 |

*Data from binding experiments using D2-CHO cells and Raclopride as the labeled ligand.
**Not a compound of the subject invention.

The animals were pretreated with reserpine (5 mg/kg, s.c.) 18 hours before the experiment. Test drugs were administered and immediately thereafter the motron activity was measured in photocell motility boxes. The rats were injected with the decarboxylase inhibitor NSD 1015 (100 mg/kg, s.c.) and killed 30 minutes later. The accumulation of DOPA in the striatum, limbic and areas and that of 5-HTP in the limbic forebrain was taken as a measure of the DA and 5-HT synthesis rates, respectively. The accumulation of DOPA in the cortex area was taken as a measure of NA synthesis rate. DA receptor agonists are known to decrease the DOPA accumulation via an activation of feedback mechanisms while DA receptor antagonists are inactive in reserpine-pretreated animals. The same theory is valid for 5-HT receptor agonists and antagonists. Dose-response curves were constructed for each compound (4–5 dose levels, n=4) and the half-maximal decrease (ED50) was calculated.

The maximal decrease of DOPA in striatum was found to be 80% and 50% for that of 5-HTP in the limbic region. I=inactive; no significant effect at the highest dose (shown in brackets). P=partial decrease; maximal decrease was not reached at the highest dose (shown in brackets). The % decrease from control is also shown. NT=not tested.

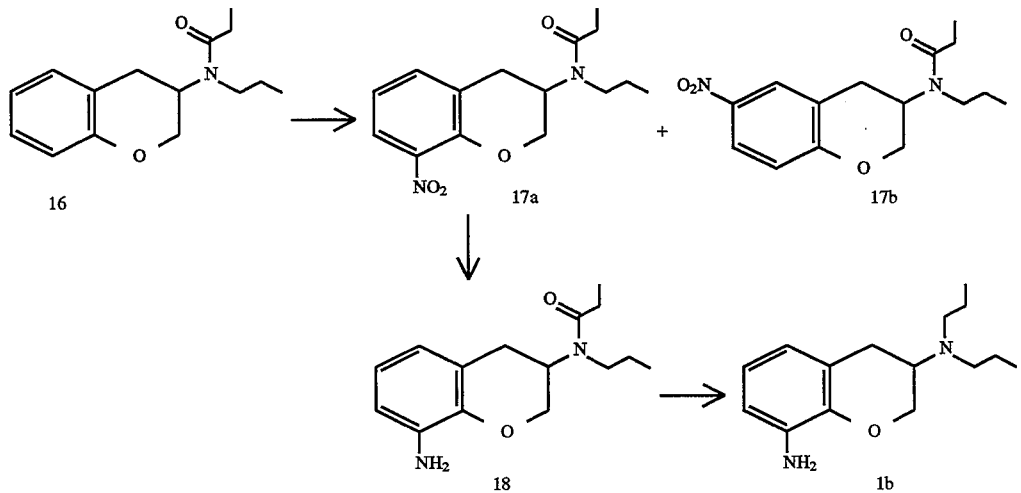

Chart A

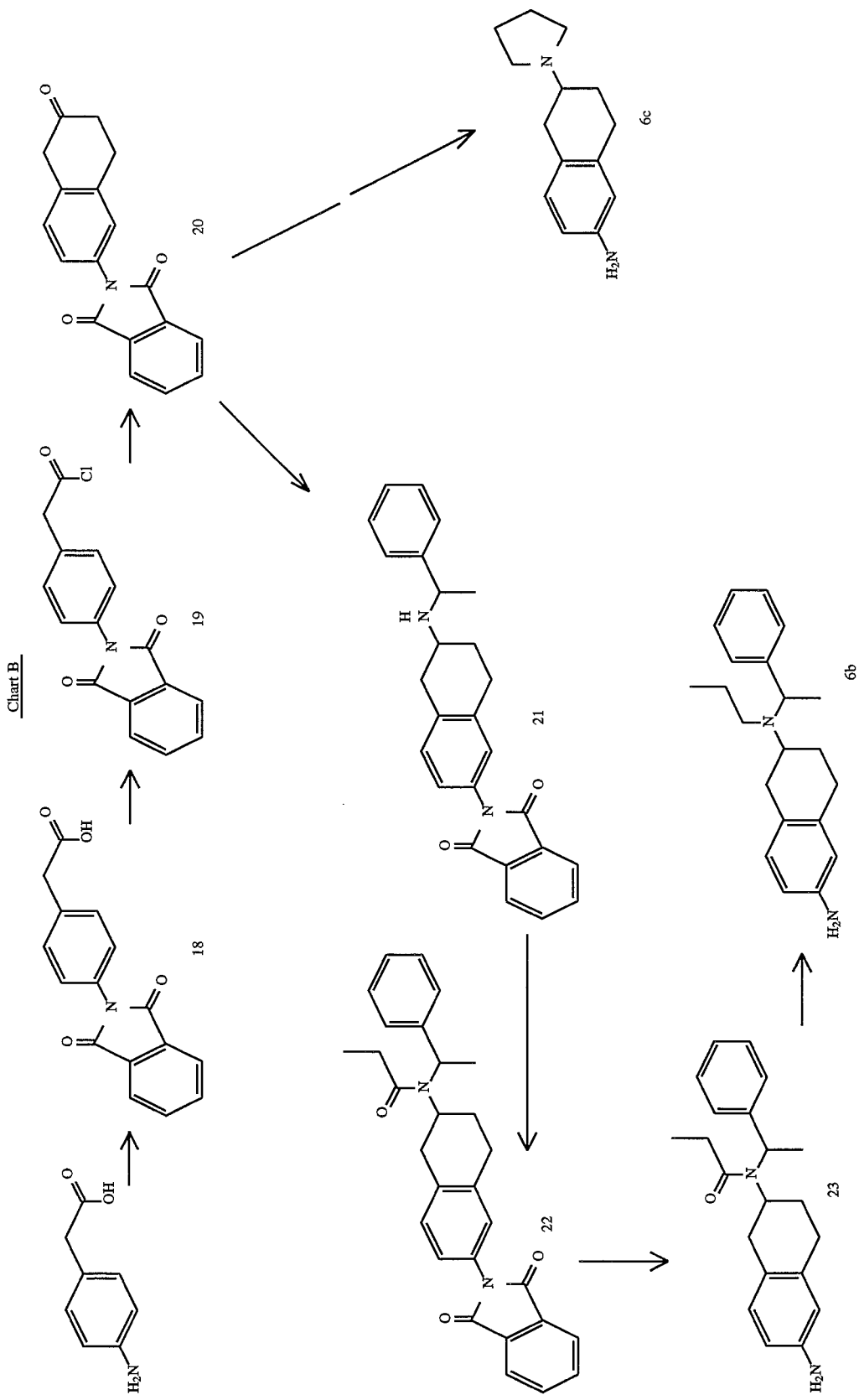

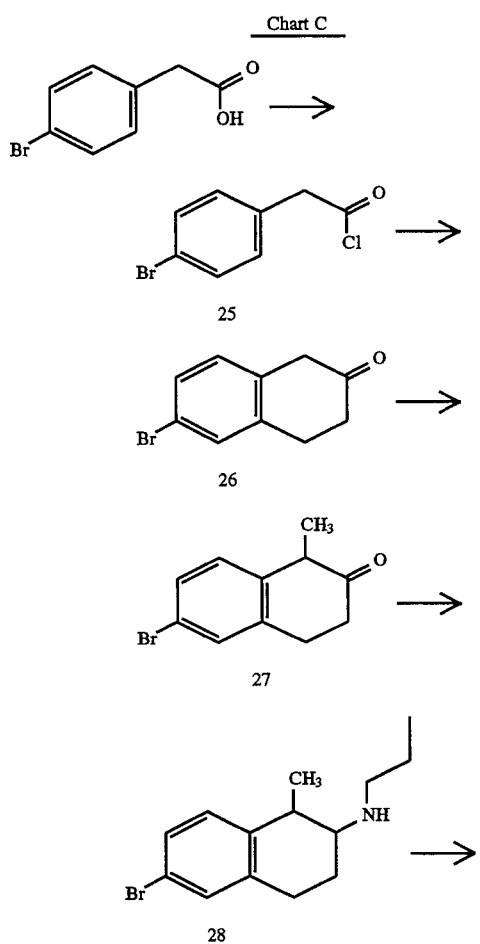
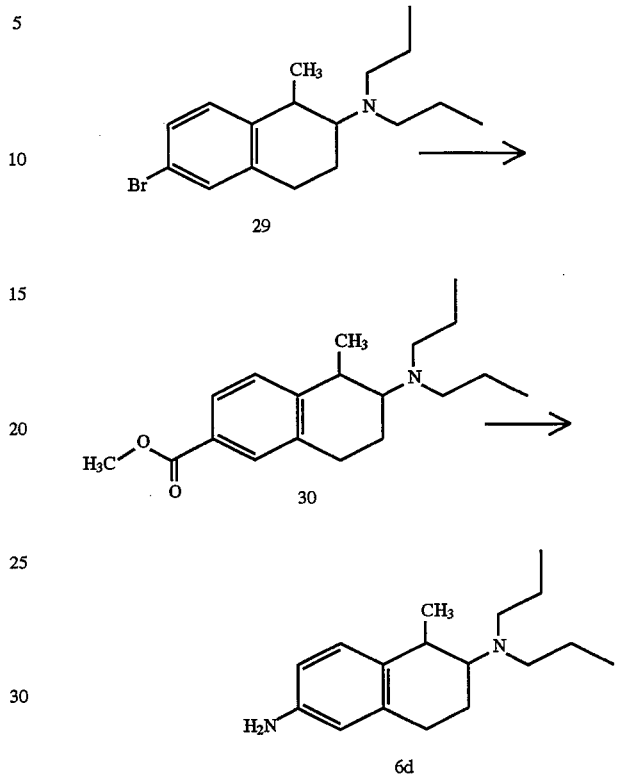
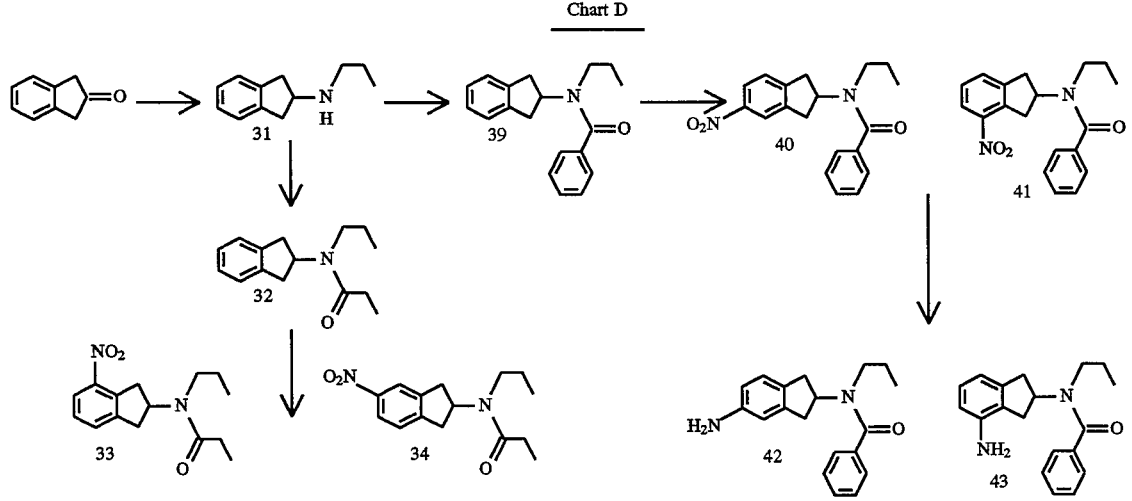

-continued
Chart D
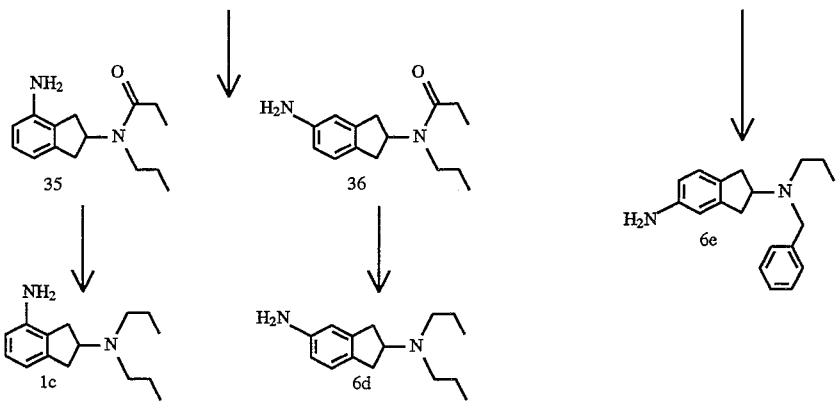
Chart E
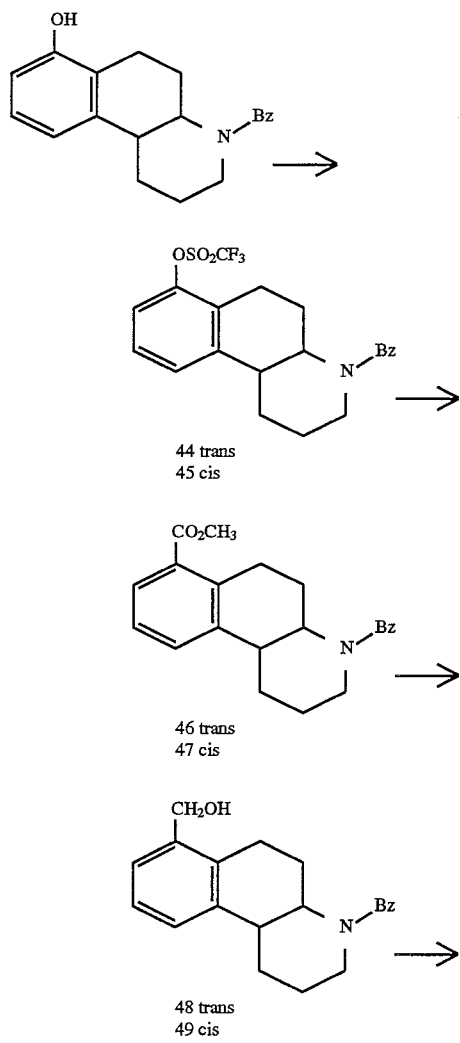
-continued
Chart E
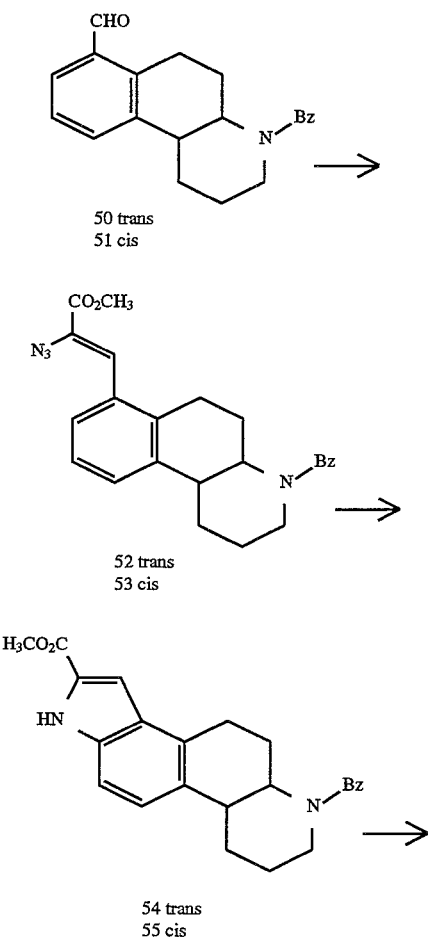

Chart E
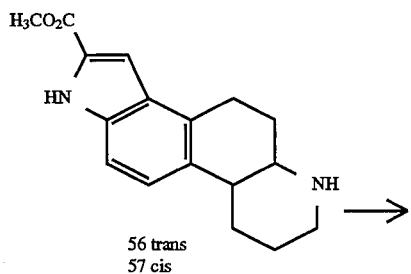
56 trans
57 cis
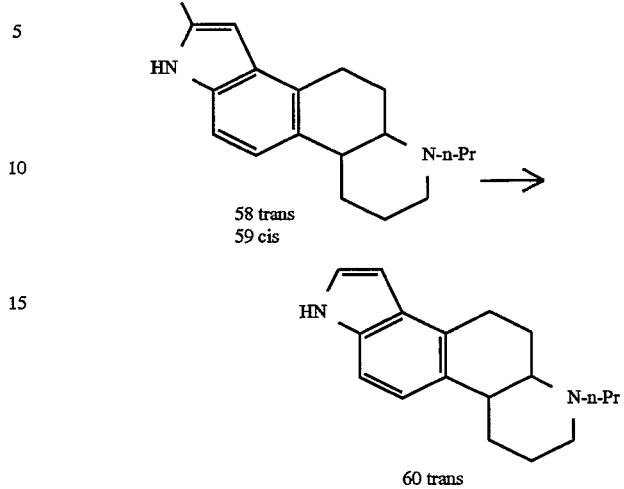
58 trans
59 cis
60 trans
Chart 1
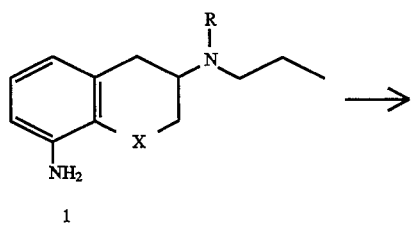
1
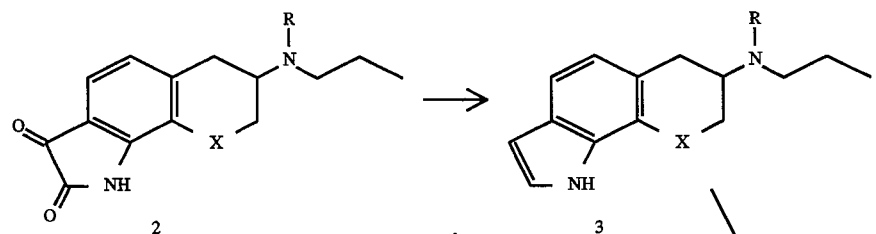
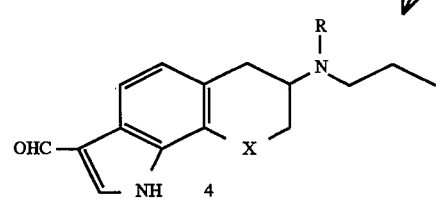
4
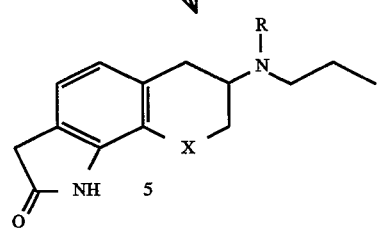
5

Chart 2
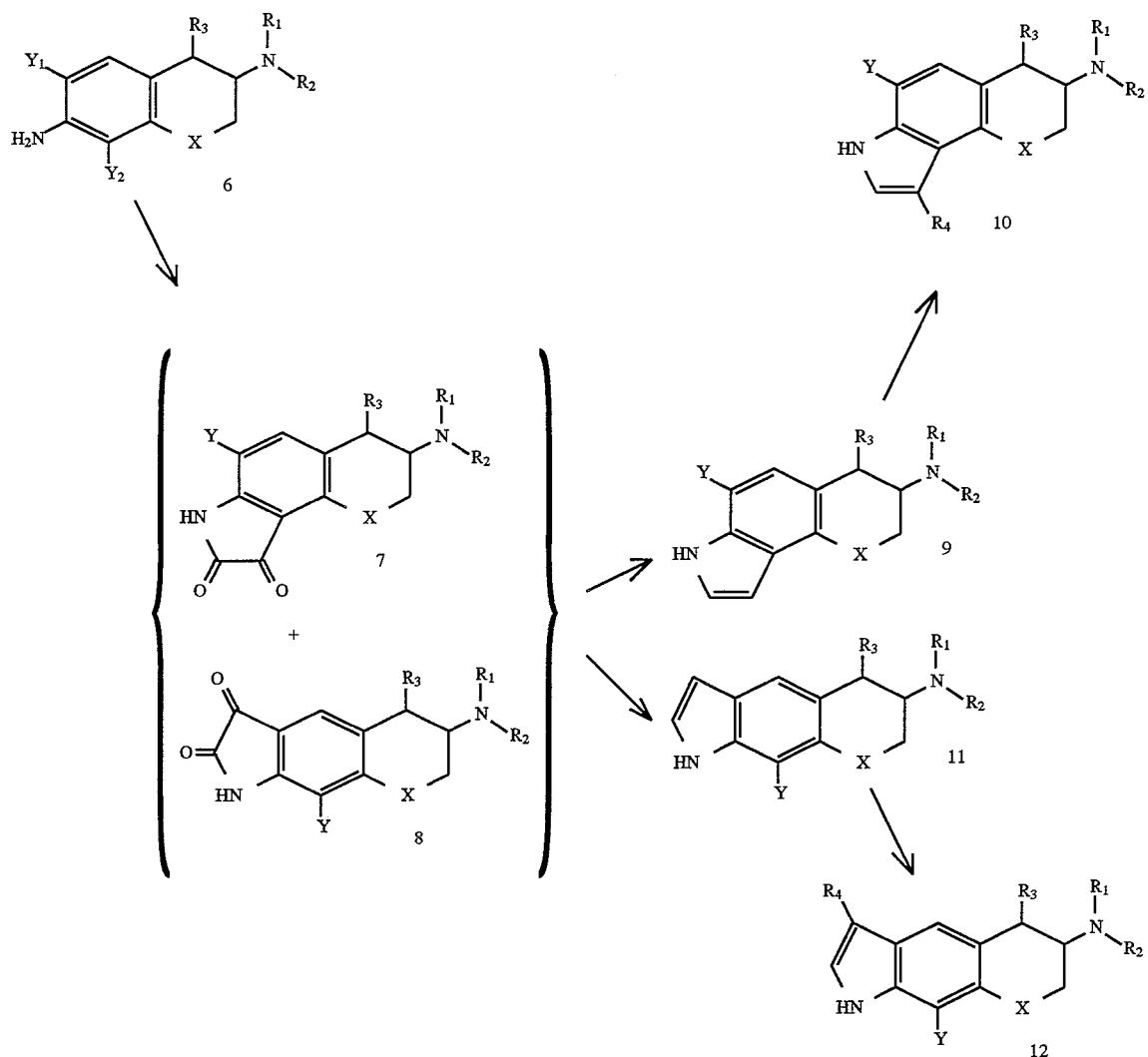
Chart 3
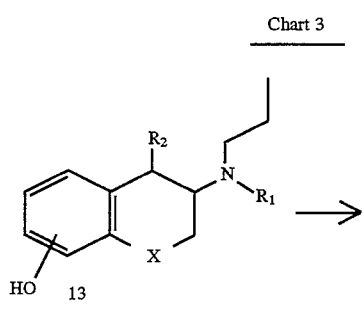

-continued
Chart 3

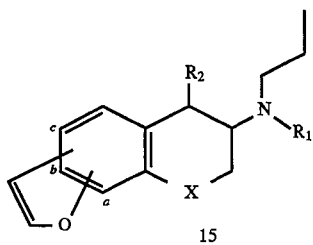

Key for the Charts

Chart 1
1a R=n-Propyl, X=—CH$_2$—
1b R=n-Propyl, X=—O—
1c R=n-Propyl, X=valence bond
2a R=n-Propyl, X=—CH$_2$—
2b R=n-Propyl, X=—O—
2c R=n-Propyl, X=valence bond
3a R=n-Propyl, X=—CH$_2$—
3b R=n-Propyl, X=—O—
3c R=n-Propyl, X=valence bond
4a R=n-Propyl, X=—CH$_2$—
4b R=n-Propyl, X=—O—
5a R=n-Propyl, X=—CH$_2$—

Chart 2
6a $R_1$=$R_2$=n-Propyl, $R_3$=H, X=—CH2—, $Y_1$=H, $Y_2$=H
6b:1 $R_1$=n-Propyl, $R_2$=1-R-Phenyl-ethyl, $R_3$=H, X=—CH2—, $Y_2$H, $Y_2$=H
6b:2 $R_1$=n-Propyl, $R_2$=1-R-Phenyl-ethyl, $R_3$=H, X=—CH2—, $Y_1$=H, $Y_2$=H
6c $R_1R_2$=13 (CH$_2$)$_4$, $R^3$=H, X=—CH2—, $Y_1$=H, $Y_2$=H
6d $R_1$=$R_2$=n-Propyl, $R_3$=CH$_3$, X=—CH2—, $Y_1$=H, $Y_2$=H
6e $R_1$=$R_2$=n-Propyl, $R_3$=CH$_3$, X=—CH2—, $Y_2$=Br, $Y_2$=H
6f $R_1$=$R_2$=n-Propyl, $R_3$—CH$_3$, X=—CH2—, $Y_2$=H, $Y_2$=Br
6g $R_1$=$R_2$=n-Propyl, $R_3$=H, X=valence bond, $Y_1$=H, $Y_2$=H
6h $R_1$=n-Propyl, $R_2$=-benzyl, $R_3$=H, X=valence bond, $Y_1$=H, $Y_2$=H
7a $R_1$=$R_2$=n-Propyl, $R_3$=H, X=—CH2—, Y=H
7b:1 $R_1$=n-Propyl, $R_2$=1-R-Phenyl-ethyl, $R_3$H, X=—CH2—, Y=H, leading to 9a:1
7b:2 $R_1$=n-Propyl, $R_2$=1-R-Phenyl-ethyl, $R_3$=H, X=—CH2—, Y=H, leading to 9a:2
7c $R_1R_2$=—(CH$_2$)$_4$—, $R_3$=H, X=—CH2—, Y=H
7d $R_1$=$R_2$=n-Propyl, $R_3$=CH$_3$, X=CH2—, Y=H
7e $R_1$=$R_2$=n-Propyl, $R_3$=CH$_3$, X=—CH2—, Y=Br
7f $R_1$=$R_2$=n-Propyl, $R_3$=H, X=valence bond, Y=H
7g $R_1$=n-Propyl, $R_2$=benzyl, $R_3$=H, X=valence bond, Y=H
8a $R_1$=$R_2$=n-Propyl, $R_3$=H, X=—CH2—, Y=H
8b:1 $R_2$=n-Propyl, $R_2$=1-R-Phenyl-ethyl, $R_3$=H, X=—CH2—, Y=H
8b:2 $R_1$=n-Propyl, $R_2$=1-R-Phenyl-ethyl, $R_3$=H, X=—CH2—, Y=H
8d $R_1$=$R_2$=n-Propyl, $R_3$=CH$_3$, X=—CH2—, Y=H
8e $R_1$=$R_2$=n-Propyl, $R_3$=CH$_3$, X=—CH2—, Y=Br
8f $R_1$=$R_2$=n-Propyl, $R_3$=H, X=valence bond, Y=H
8g $R_1$=n-Propyl, $R_2$=benzyl, $R_3$=H, X=valence bond, Y=H
9a $R_1$=$R_2$=n-Propyl, $R_3$=H, X=—CH2—, Y=H
9a:1 $R_1$=$R_2$=n-Propyl, $R_3$H, X=—CH2—, Y—H, (−)-enantiomer of 9a
9a:2 $R_1$=$R_2$=n-Propyl, $R_3$=H, X=—CH$_2$—, Y=H, (+)-enantiomer of 9a
9b:1 $R_1$=n-Propyl, $R_2$=1-R-Phenyl-ethyl, $R_3$=H, X=—CH$_2$—, Y=H, leading to 9a:1
9b:2 $R_1$=n-Propyl, $R_2$=1-R-Phenyl-ethyl, $R_3$=H, X=—CH2—, Y=H, leading to 9a:2
9c $R_1R_2$=—(CH$_2$)$_4$—, $R_3$=H, X=—CH2—, Y=H
9d $R_1R_2$=n-Propyl, $R_3$=CH$_3$, X=—CH2—, Y=H
9e:1 =$R_1$=n-Propyl, $R_2$=$R_3$=H, X=—CH2—, Y=H, leading to 9a:1
9e:2 $R_1$=n-Propyl, $R_2$=$R_3$=H, X=—CH2—, Y=H, leading to 9a:2
9f $R_1$=n-Propyl, $R_2$=methyl, $R_3$=H, X=—CH2—, Y=H
9g $R_1$=n-Propyl, $R_2$=2-thiophenethyl, $R_3$=H, X=—CH2—, Y=H
9h $R_1$=n-Propyl, $R_2$=cyclobutylmethyl, $R_3$=H, X=—CH2—, Y=H
9i $R_1$=$R_2$=n-Propyl, $R_3$=H, X=—CH2—, Y=Br
9j $R_1$=$R_2$=n-Propyl, $R_3$=H, X=valence bond, Y=H
9k $R_1$=n-Propyl, $R_2$=benzyl, $R_3$=H, X=valence bond, Y=H
10a:1 $R_1$=$R_2$=n-Propyl, $R_3$=H, $R_4$=CHO, $R_5$=H, X=—CH2—, Y=H
10a:2 $R_1R_2$=n-Propyl, $R_3$=H, $R_4$=CHO, $R_5$=H, X=—CH2—, Y=H (+)-enantiomer of 10a
10b $R_1$=$R_2$=n-Propyl, $R_3$=H, $R_4$=CN, X=—CH2—, Y=H
10d $R_1$=$R_2$=n-Propyl, $R_3$=CH$_3$, $R_4$=CHO, X=—CH2—, Y=H
10e $R_1$=n-Propyl, $R_2$=methyl, $R_3$=H, $R_4$=SMe, X=—CH2—, Y=H
10f $R_1$=n-Propyl, $R_2$=2-thiophenethyl, $R_3$=H, $R_4$=CHO, X=—CH$_2$—, Y=H
10g $R_1$=n-Propyl, $R_2$=cyclobutylmethyl, $R_3$32 H, $R_4$=CHO, X=—CH2—, Y=H
10h $R_1$=$R_2$=n-Propyl, $R_3$=H, $R_4$=H, X=—CH2—, Y=H
10i $R_1$=$R_2$=n-Propyl, $R_3$=H, $R_4$=COCF$_3$, X=—CH2—, Y=H
10j $R_1$=$R_2$=n-Propyl, $R_3$=H, $R_4$=COEt, X=—CH2—, Y=H
10k $R_1$=$R_2$=n-Propyl, $R_3$=H, $R_4$=COMe, X=—CH$_2$—, Y=H
11a $R_1$=$R_2$=n-Propyl, $R_3$=H, X=—CH2—, Y=H
11b $R_1$=$R_2$=n-Propyl, $R_3$=H, X=—CH2—, Y=Br
11d $R_1$=$R_2$=n-Propyl, $R_3$=CH$_3$, X=—CH2—, Y=H
11e $R_1$=$R_2$=n-Propyl, $R_3$=H, X=valence bond, Y=H
11f $R_1$=n-Propyl, $R_2$=benzyl, $R_3$=H, X=valence bond, Y=H
11g $R_1$=n-Propyl, $R_2$=H, $R_3$=H, X=valence bond, Y=H
11h $R_1$=n-Propyl, $R_2$=cyclopropylmethyl, $R_3$=H, X=valence bond, Y=H
11i $R_1$=n-Propyl, $R_2$=(4-Fluoro-phenyl)ethyl, $R_3$=H, X=valence bond, Y=H
12a $R_1$=$R_2$=n-Propyl, $R_3$=H, $R_4$=CHO, X=—CH2—, Y=H
12b $R_1$=$R_2$=n-Propyl, $R_3$=H, $R_4$=H=, X=—CH2—, Y=H
12c $R_1$=$R_2$=n-Propyl, $R_3$=H, $R_4$=COEt, X=—CH2—, Y=H
12d $R_1$=$R_2$=n-Propyl, $R_3$=H, $R_4$=CHO, X=—CH2—, Y=Br
12e $R_1$=$R_2$=n-Propyl, $R_3$=H, $R_4$=CHO, X=valence bond, Y=H
12f $R_1$=$R_2$=n-Propyl, $R_3$=H, $R_4$=COEt, X=valence bond, Y=H
12g $R_1$=$R_2$=n-Propyl, $R_3$=H, $R_4$COPh, X=valence bond, Y=H
12h $R_1$=n-Propyl, $R_2$=cyclopropylmethyl, $R_3$=H, $R_4$=COEt, X=valence bond, Y=H
12i $R_1$=n-Propyl, $R_2$=cyclopropylmethyl, $R_3$=H, $R_4$n-Propyl, X=valence bond, Y=H
12j $R_1$=n-Propyl, $R_2$=(4-Fluoro-phenyl)ethyl, $R_3$=H, $R_4$=n-Propyl, X=valence bond, Y=H Chart 3
13a $R_1$=n-Propyl, $R_2$=H, X=—CH$_2$—, a=—O—
13b $R_1$=n-Propyl, $R_2$=H, X=—CH$_2$—, b=—O—
13c $R_1$=n-Propyl, $R_2$=Me, X=—CH$_2$—, a=—O—
13d $R_1$=n-Propyl, $R_2$=Me, X=valence bond, a=—O—
13e $R_1$=n-Propyl, $R_2$=Me, X=valence bond, b=—O—

14a $R_1$=n-Propyl, $R_2$=H, X=—$CH_2$—, a=—O—
14b $R_1$=n-Propyl, $R_2$=H, X=$CH_2$—, b=—O—
14c $R_1$=n-Propyl, $R_2$=Me, X=—$CH_2$—, a=—O—
14d $R_1$=n-Propyl, $R_2$=Me, X=valence bond, a=—O—
14e $R_1$=n-Propyl, $R_2$=Me, X=valence bond, b=—O—
15a $R_1$=n-Propyl, $R_2$=H, X=—$CH_2$—, a=—O—, b=—C—
15b $R_1$=n-Propyl, $R_2$=H, X=—$CH_2$—, b=—O—, a=—C—
15c $R_1$=n-Propyl, $R_2$=H, X=—$CH_2$—, b=—O—, c=—C—
15d $R_1$=n-Propyl, $R_2$=Me, X=—$CH_2$—, a=—O—, b=—C—
15e $R_1$=n-Propyl, $R_2$=Me, X=valence bond, a=—O—, b=—C—
15f $R_1$=n-Propyl, $R_2$=Me, X=valence bond, b=—O—, a=—C—
15g $R_1$=n-Propyl, $R_2$=Me, X=valence bond, b=—O—, c=—C—

What is claimed is:

1. A compound of Formula I or pharmaceutically acceptable salts thereof:

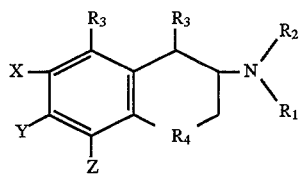

where Z is $R_3$ then X and Y form (a), or where X is $R_3$ then Y and Z form (a) or (b)

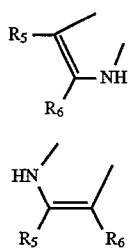

$R_1$ and $R_2$ are independently hydrogen, $C_{1-6}$ alkyl, $C_{3-7}$ cycloalkyl, —$CH_2$—$C_{3-7}$ cycloalkyl, phenyl (optionally substituted with halogen or $C_{1-6}$ alkyl), -thiophenyl (optionally substituted with halogen or $C_{1-6}$ alkyl), or $C_{1-6}$ alkyl phenyl;

$R_3$ are independently hydrogen, halogen, —O—$C_{1-6}$ alkyl or $C_{1-6}$ alkyl;

$R_4$ is a valence bond, $CH_2$ or oxygen;

$R_5$ and $R_6$ are independently hydrogen, sulfur, —S—$C_{1-6}$ alkyl, halogen, $CON(R_3)_2$, —$COCF_3$, —CO—$C_{1-6}$ alkyl, —CO phenyl, oxygen, —CHO or CN; except that when Y and Z form (b), $R_1$ and $R_2$ are hydrogen or a $C_{1-6}$ alkyl and $R_3$ is hydrogen, then at least one of $R_5$ and $R_6$ must be other than hydrogen, alkyl or oxygen.

2. The compound of claim 1 wherein $R_1$ and $R_2$ are hydrogen.

3. The compound of claim 1 wherein $R_5$ and $R_6$ are oxygen.

4. The compound of claim 1 wherein X is hydrogen and Y and Z form (a).

5. The compound of claim 4 wherein $R_5$ and $R_6$ are both hydrogen or oxygen.

6. The compound of claim 1 wherein $R_4$ is $CH_2$.

7. The compound of claim 1 wherein $R_4$ is oxygen.

8. The compound of claim 7 wherein X is hydrogen and Y and Z form (a).

9. A method for stimulating dopamine-receptor activity in mammals comprising: administering to a mammal in need thereof a therapeutic amount of a compound of Formula I or a pharmaceutically acceptable salts thereof

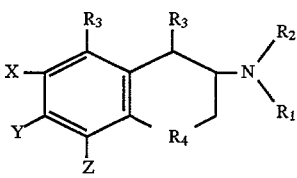

where Z is $R_3$ then X and Y form (a), or where X is $R_3$ then Y and Z form (a) or (b)

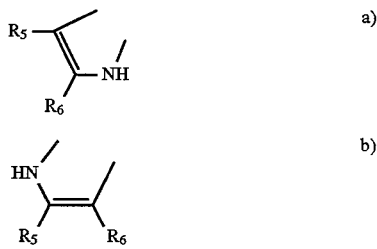

$R_1$ and $R_2$ are independently hydrogen, $C_{11-6}$ alkyl, $C_{3-7}$ cycloalkyl, —$CH_2$—$C_{3-7}$ cycloalkyl, phenyl (optionally substituted with halogen or $C_{1-6}$ alkyl), -thiophenyl (optionally substituted with halogen or $C_{1-6}$ alkyl), or $C_{1-6}$ alkyl phenyl;

$R_3$ are independently hydrogen, halogen, —O—$C_{1-6}$ alkyl or $C_{1-6}$ alkyl;

$R_4$ is a valence bond, $CH_2$ or oxygen;

$R_5$ and $R_6$ are independently hydrogen, sulfur, —S—$C_{1-6}$ alkyl, halogen, $CON(R_3)_2$, —$COCF_3$, —CO—$C_{1-6}$ alkyl, —CO phenyl, oxygen, —CHO or CN; except that when Y and Z form (b), $R_1$ and $R_2$ are hydrogen or a $C_{1-6}$ alkyl and $R_3$ is hydrogen, then at least one of $R_5$ and $R_6$ must be other than hydrogen, alkyl or oxygen.

* * * * *